United States Patent
Li et al.

(10) Patent No.: US 12,371,403 B2
(45) Date of Patent: *Jul. 29, 2025

(54) GENERATION OF PEROXYHYDROXYCARBOXYLIC ACID AND THE USE THEREOF

(71) Applicant: ECOLAB USA INC., Saint Paul, MN (US)

(72) Inventors: Junzhong Li, Saint Paul, MN (US); Allison Prideaux, Saint Paul, MN (US); Richard Staub, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/485,955

(22) Filed: Oct. 12, 2023

(65) Prior Publication Data

US 2024/0059651 A1 Feb. 22, 2024

Related U.S. Application Data

(63) Continuation of application No. 17/248,562, filed on Jan. 29, 2021, now Pat. No. 11,820,737.

(60) Provisional application No. 62/968,597, filed on Jan. 31, 2020.

(51) Int. Cl.
C07C 407/00 (2006.01)
A01N 37/16 (2006.01)
C12P 7/42 (2006.01)

(52) U.S. Cl.
CPC ............ *C07C 407/00* (2013.01); *A01N 37/16* (2013.01); *C07C 407/006* (2013.01); *C12P 7/42* (2013.01)

(58) Field of Classification Search
None
See application file for complete search history.

(56) References Cited

U.S. PATENT DOCUMENTS

| | | | |
|---|---|---|---|
| 1,065,774 A | 6/1913 | Breault | |
| 3,625,975 A | 12/1971 | Crampton et al. | |
| 3,994,969 A | 11/1976 | Vanlautem et al. | |
| 4,115,309 A | 9/1978 | Krause et al. | |
| 4,870,192 A | 9/1989 | Chang et al. | |
| 5,151,212 A | 9/1992 | Bell et al. | |
| 5,411,673 A | 5/1995 | Agar et al. | |
| 5,665,891 A | 9/1997 | Brown et al. | |
| 5,743,514 A | 4/1998 | Rees | |
| 5,972,237 A | 10/1999 | Müller et al. | |
| 6,103,286 A | 8/2000 | Gutzmann et al. | |
| 6,139,756 A | 10/2000 | Fuchs et al. | |
| 6,165,957 A | 12/2000 | Vitomir | |
| 6,387,858 B1 | 5/2002 | Shah et al. | |
| 6,627,594 B1 | 9/2003 | James et al. | |
| 6,627,657 B1 * | 9/2003 | Hilgren ................. A01N 37/16 514/568 |
| 6,962,714 B2 | 11/2005 | Hei et al. | |
| 7,384,787 B2 * | 6/2008 | Kazlauskas ............ C12N 9/18 435/198 |
| 7,666,354 B2 | 2/2010 | Kawakami et al. | |
| 7,771,737 B2 | 8/2010 | Man et al. | |
| 8,020,520 B2 | 9/2011 | Hilgren et al. | |
| 8,802,086 B2 | 8/2014 | Herdt et al. | |
| 8,841,098 B2 | 9/2014 | Payne et al. | |
| 8,846,107 B2 * | 9/2014 | Li ........................ C07C 409/24 562/2 |
| 8,865,435 B2 | 10/2014 | Payne et al. | |
| 8,865,436 B2 | 10/2014 | Payne et al. | |
| 8,877,240 B1 | 11/2014 | Moore | |
| 8,969,282 B2 | 3/2015 | Heisig et al. | |
| 9,084,421 B2 | 7/2015 | McSherry | |
| 9,414,609 B1 | 8/2016 | Bullard et al. | |
| 9,701,931 B2 | 7/2017 | Moore | |
| 9,708,256 B2 | 7/2017 | McSherry et al. | |
| 9,862,915 B2 | 1/2018 | Stolte et al. | |
| 10,010,075 B2 | 7/2018 | Herdt et al. | |
| 10,278,392 B2 | 5/2019 | Bolduc et al. | |
| 10,285,400 B2 | 5/2019 | Lei et al. | |
| 10,285,401 B2 | 5/2019 | McSherry et al. | |

(Continued)

FOREIGN PATENT DOCUMENTS

DE 1800069 A1 5/1970
DE 4231466 A1 3/1994

(Continued)

OTHER PUBLICATIONS

International Searching Authority in connection with PCT/US2021/015602 filed Jan. 29, 2021, "The International Search Report and the Written Opinion of the International Searching Authority, or the Declaration", 10 pages, mailed May 11, 2021.

Rusch et al., "Biocatalytic peroxy acid formation for disinfection", Journal of Molecular Catalysis B: Enzymatic, vol. 19-20, pp. 499-505, Dec. 2, 2002.

European Patent Office, "European Search Report", issued in connection to Application No. 21202775.9, 6 pages, mailed Feb. 21, 2022.

Gonzalez et al., "Efficacy of Postharvest Treatments for Reduction of Molds and Decay in Fresh Michigan Chestnuts", Acta Horticulturae, https://www.ishs.org/ishs-article/866_76, 5 pages, 2010.

*Primary Examiner* — Christian L Fronda
(74) *Attorney, Agent, or Firm* — McKee, Voorhees & Sease, PLC

(57) ABSTRACT

Peroxyhydroxycarboxylic acid forming compositions and methods for forming peroxyhydroxycarboxylic acids, preferably in situ, using the peroxyhydroxycarboxylic acid forming compositions are disclosed. Methods of using the peroxyhydroxycarboxylic acids, including for treating a surface or a target in need of antimicrobial or sanitizing treatment are also disclosed. Particular applications of using odor-free, low volatility peroxyhydroxycarboxylic acid sanitizers for direct food contact are disclosed.

20 Claims, 9 Drawing Sheets

(56) References Cited

U.S. PATENT DOCUMENTS

| | | |
|---|---|---|
| 10,487,297 B2 | 11/2019 | Moore |
| 11,739,058 B2 * | 8/2023 | Li .......................... A01P 1/00 562/6 |
| 11,820,737 B2 * | 11/2023 | Li .......................... C12P 7/42 |
| 2003/0185902 A1 | 10/2003 | Hei et al. |
| 2004/0033923 A1 | 2/2004 | McClung |
| 2005/0042261 A1 | 2/2005 | Hasenoehrl et al. |
| 2006/0286651 A1 * | 12/2006 | Kazlauskas ............. C12N 9/18 435/198 |
| 2008/0251105 A1 | 10/2008 | Toussant et al. |
| 2009/0061017 A1 | 3/2009 | Pedersen et al. |
| 2009/0069545 A1 | 3/2009 | Anderson et al. |
| 2009/0285871 A1 | 11/2009 | Cunningham et al. |
| 2010/0196503 A1 | 8/2010 | Heisig et al. |
| 2012/0213864 A1 | 8/2012 | McClung |
| 2013/0251590 A1 | 9/2013 | Golden et al. |
| 2016/0021888 A1 | 1/2016 | Burke et al. |
| 2016/0174553 A1 | 6/2016 | Matta et al. |
| 2016/0295859 A1 | 10/2016 | Chan et al. |
| 2017/0172145 A1 | 6/2017 | Sherry et al. |
| 2017/0173619 A1 | 6/2017 | Sherry et al. |
| 2018/0042249 A1 | 2/2018 | Bullard et al. |
| 2018/0020881 A1 | 7/2018 | Joshi |
| 2020/0214288 A1 | 7/2020 | Osei-Owusu |
| 2021/0238135 A1 | 8/2021 | Li et al. |
| 2022/0251037 A1 | 8/2022 | Li et al. |

FOREIGN PATENT DOCUMENTS

| | | |
|---|---|---|
| EP | 0682696 A1 | 11/1995 |
| EP | 1061071 A1 | 12/2000 |
| EP | 1265486 B1 | 12/2002 |
| EP | 3984365 A1 | 4/2022 |
| GB | 1070323 | 6/1967 |
| GB | 1577396 A | 10/1980 |
| JP | 6279409 B2 | 1/2018 |
| KR | 101582221 B1 | 1/2016 |
| WO | 9302973 A1 | 2/1993 |
| WO | 0152827 A1 | 7/2001 |
| WO | 0170030 A2 | 9/2001 |
| WO | 2021154959 A1 | 8/2021 |

\* cited by examiner

GENERATION OF PEROXYHYDROXYCARBOXYLIC ACID AND THE USE THEREOF

CROSS-REFERENCE TO RELATED APPLICATION

This application is a Continuation Application of U.S. Ser. No. 17/248,562, filed on Jan. 29, 2021, which claims priority under 35 U.S.C. § 119 to Provisional Application U.S. Ser. No. 62/968,597, filed on Jan. 31, 2020. The Provisional Application U.S. Ser. No. 62/968,597 is herein incorporated by reference in its entirety.

FIELD OF THE INVENTION

The present disclosure relates generally to peroxyhydroxycarboxylic acid forming compositions and methods for forming peroxyhydroxycarboxylic acids, preferably in situ, using the peroxyhydroxycarboxylic acid forming compositions. The present disclosures also relates to methods of using the peroxyhydroxycarboxylic acids, including for treating a surface or a target in need of antimicrobial treatment. Applications of using odor-free, low volatility peroxyhydroxycarboxylic acid sanitizers include use as direct food contact sanitizers.

BACKGROUND OF THE INVENTION

Peroxycarboxylic acid compositions are generally made through an acid catalyzed equilibrium reaction. Most often, the peroxycarboxylic acids are generated in a chemical plant, and then shipped to customers for on-site use. Due to the limited storage stability of peroxycarboxylic acids, the peroxycarboxylic acids must be packed in special containers and shipped under strict Department of Transportation (DOT) guidelines. Further, excess amounts of reagents (e.g., acids, oxidizing agents, and stabilizers) are present in the compositions during shipping to prevent decomposition. For these reasons there is ongoing demand for the on-site generation of peroxycarboxylic acids.

Peroxycarboxylic acids are increasingly used as antimicrobials, sanitizing agents, and bleaching agents in various applications, owing to their high efficacy against a broad spectrum of microorganisms, color safe property, low residues and nontoxic nature of their decomposition products. Peracetic acid is the most commonly used peroxycarboxylic acid. It is increasingly used as a direct food contact sanitizer owing to its broad antimicrobial efficiency and most importantly it leaves no toxic residues as it decomposes into acetic acid, water and oxygen. However, there are disadvantages to its use, namely peracetic acid has relatively high vapor pressure, has strong pungent odor, and can be irritative to tissue when inhaled. As a result, in the United States the Occupational Safety and Health Administration (OSHA) has set in place concentration limits for air borne concentrations of peracetic acid. For example, in locations where peracetic acid is applied in an open system at relatively high concentrations and used in large quantities (e.g. use in poultry processing plants), the concentration of peracetic acid in the air could cause significant safety issues to workers. Accordingly, there is a need to find alternative efficacious and odorless antimicrobials that do not leave toxic residues, and at the same time have very low vapor pressure.

Hydroxycarboxylic acids, including alphahydroxycarboxylic acids such as lactic acid, are readily available compounds that can be made from food grade raw materials. They are extensively used in the food industry as acidulants as well as antimicrobial reagents. The hydroxycarboxylic acids have very low vapor pressure and have no irritative odor. Although alphahydroxycarboxylic acids such as lactic acid has been known to have antimicrobial properties, their antimicrobial efficacy is relatively low, requiring at least percentage levels of the compounds to achieve required efficacy. This is a significant limitation against their broad use as food safe antimicrobials. As a result, there have been attempts to boost the antimicrobial efficacy of lactic acid by transferring it to perlactic acid. Such attempts have reacted lactic with hydrogen peroxide (such as how acetic acid is used to produce peracetic acid). This has proven to be unsuccessful, as unlike the simple alkane carboxylic acids such as acetic acid, alphahydroxycarboxylic acids are weak reducing agents and therefore liable to be oxidized by hydrogen peroxide during the reaction to produce the corresponding peroxy alphahydroxycarboxylic acid. This requires high concentrations of hydrogen peroxide and the reaction can take hours to days, resulting in a lack of adaptation of its use in the industry. Further reason for a lack of adaptation and use, is that the oxidation of alphahydroxycarboxylic acid by hydrogen peroxide causes significant stability issues and some of the oxidized species may not be safe for direct food use. As a still further disadvantage conventional methods for producing peroxyhydroxycarboxylic acids, such as peroxylactic acid, result in compositions that begin decomposing as fast at the formation rate and therefore provide compositions with insufficient concentrations of the peroxyhydroxycarboxylic acid.

There is a need to seek alternative ways to generate peroxyhydroxycarboxylic acids, such as peroxylactic acid. The present disclosure addresses this and the related needs using, inter alia, peroxyhydroxycarboxylic acids having improved antimicrobial efficacy compared to the corresponding alphahydroxycarboxylic acids.

There is a further need for generating stoichiometric amounts of the peroxyhydroxycarboxylic acids, such that one mole of a lactone precursor will generate one mole of the corresponding peroxyalphahydroxycarboxylic acid plus mole of the alphahydroxycarboxylic acid.

There is a still further need for such ways to generate peroxyhydroxycarboxylic acids in faster reactions that take minutes as opposed to hours or days.

Still further needs for in situ generation of peroxyhydroxycarboxylic acids that can be subsequently used on site or promptly after generation to avoid oxidation of the alphahydroxycarboxylic acids.

BRIEF SUMMARY OF THE INVENTION

The present disclosure relates generally to peroxyalphahydroxycarboxylic acid forming compositions, methods for forming peroxyalphahydroxycarboxylic acids, preferably in situ, using the peroxyalphahydroxycarboxylic acid forming compositions, and methods, and the uses of the peroxyalphahydroxycarboxylic acids, preferably in situ, for treating a surface or a target.

In embodiments, a method for forming a peroxyhydroxycarboxylic acid comprises: contacting reagents comprising a lactone of an alphahdroxycarboxylic acid with an alkalinity source and hydrogen peroxide or a substance that generates hydrogen peroxide when in contact with a liquid, to form a liquid that comprises the peroxyhydroxycarboxylic acid and has a pH below about 7 within about 5 minutes after the contact between the reagents; and generating at least about 1 ppm of the peroxyhydroxycarboxylic acid at the point of contacting to within less than 1 minute.

In embodiments, a peroxyhydroxycarboxylic acid forming composition comprises: a first reagent that comprises a lactone of an alphahdroxycarboxylic acid, and a second reagent that comprises an alkalinity source, a third reagent that comprises hydrogen peroxide or that comprises a substance that generates hydrogen peroxide when in contact with a liquid; and optionally water or a solvent if the first, second and/or third reagents are powders; wherein said reagents are provided as powders and/or liquids, and wherein the powder reagents are combined into a premix and the liquid reagents are kept separately from the powder reagents prior to contacting to generate the peroxyhydroxycarboxylic acid; and wherein the combination of the reagents react to form a liquid that comprises the peroxyhydroxycarboxylic acid and has a pH below about 7 within about 5 minutes after the contact between said reagent.

In embodiments, a method for treating a target comprises contacting a target with an effective amount of peroxyhydroxycarboxylic acid or the peroxyhydroxycarboxylic acid produced according to the methods described herein, to form a treated target composition, wherein said treated target composition comprises from about 0.1 ppm to about 10,000 ppm of said peroxyhydroxycarboxylic acid, and said contacting lasts for sufficient time to bleach, remove soils, disinfect and/or stabilize or reduce microbial population in and/or on said target or said treated target composition.

In embodiments a peroxyalphahydroxycarboxylic acid composition comprises: peroxylactoyllactic acid; and peroxylactic acid.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
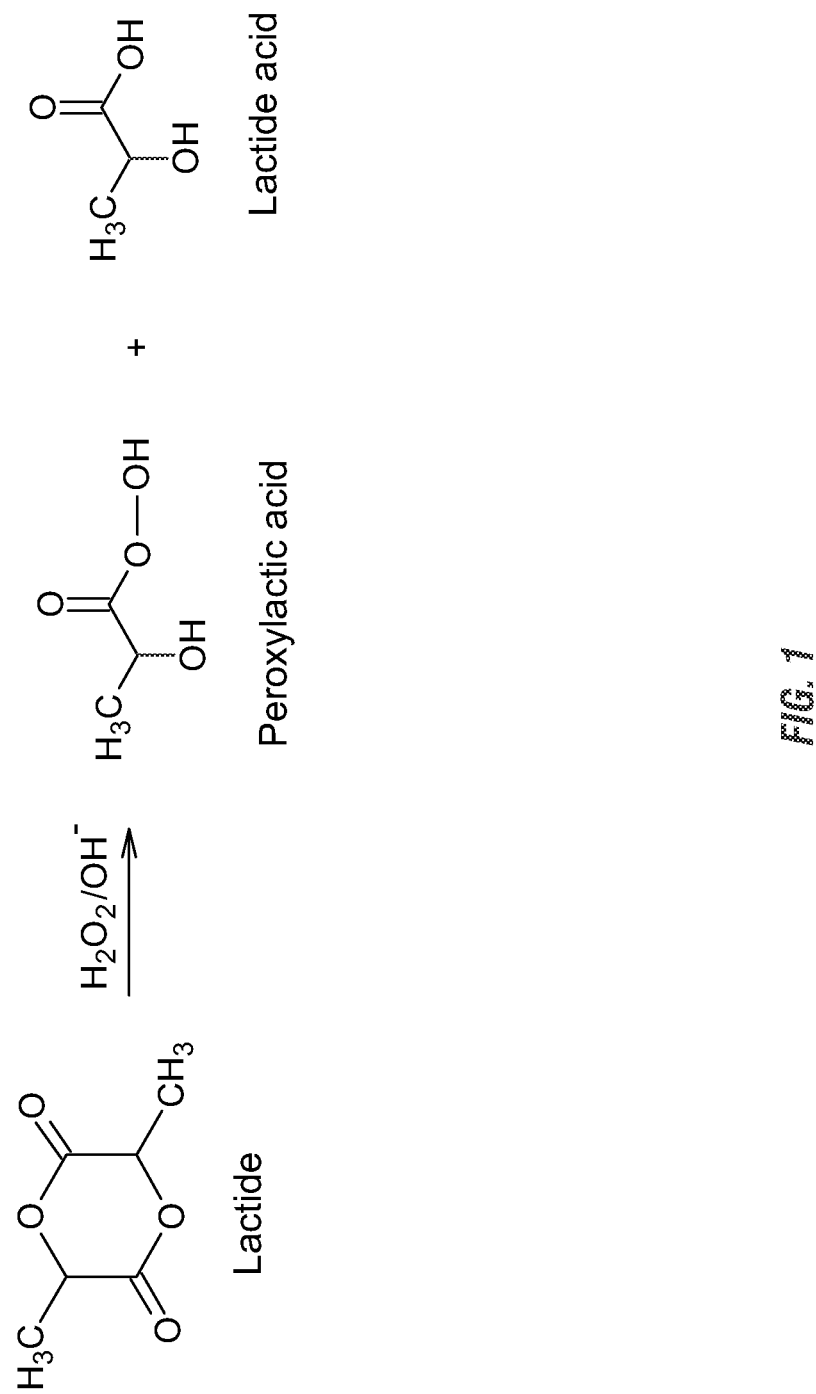
FIG. 1 illustrates perhydrolysis of lactide to form peroxylactic acid according to embodiments described herein.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular peroxyalphahydroxycarboxylic acid forming compositions, methods for forming peroxyalphahydroxycarboxylic acids, the formed peroxyalphahydroxycarboxylic acid and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference. So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food or beverage processing, preparation, or storage activity. Food processing surface is intended to encompass all surfaces used in brewing (including beer brewing and preparation of liquors and spirits) and winemaking processes (e.g., bright beer tanks and lines, fermentation vessels, mash tuns, bottling equipment, pipes, and storage vessels). Examples of food processing surfaces include surfaces of food processing or preparation equipment (e.g., boiling, fermenting, slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food antispoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

The term "hard surface" refers to a solid, substantially non-flexible surface such as a countertop, tile, floor, wall, panel, window, plumbing fixture, kitchen and bathroom furniture, appliance, engine, circuit board, instruments, and dishes. Hard surfaces may include for example, health care surfaces and food processing surfaces.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "peroxyalphahydroxycarboxylic acid" (or peracid) includes any compound of the formula R—CR'(OH)—(COOOH)n in which R and R' can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein. As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or 'carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, C1-4 alkyl, C1-4 alkenyl, C1-4 alkoxy, amino, carboxy, halo, nitro, cyano, —SO3H, phosphono, or hydroxy. When alkyl, alkenyl, alicyclic group, or heterocyclic group is substituted, preferably the substitution is C1-4 alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —SO3H, phosphono, or hydroxy. When aryl, aralkyl, or heteroaryl is substituted, preferably the substitution is C1-4 alkyl, halo, nitro, amido, hydroxy, carboxy, sulpho, or phosphono. In one embodiment, R includes aryl substituted with C1-4 alkyl.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

Peroxyalphahydroxycarboxylic Acid Forming Compositions

Peroxyalphahydroxycarboxylic acid forming compositions are provided to generate peroxyalphahydroxycarboxylic acids that have a low vapor pressure and are odorless are therefore particularly well suited for applications of use for contacting certain surfaces and targets. Exemplary peroxyalphahydroxycarboxylic acids are shown in Table 1 along with corresponding vapor pressure and odor profile. The methods described herein provide peroxyalphahydroxycarboxylic acid forming compositions that have low vapor pressure and are odorless to be suitable for applications of use where they are in direct contact with food, hard surfaces and human tissue (e.g. inhaled). As defined herein, low vapor pressure refers to a compound having less than about 1 KPa vapor pressure at 20° C. In preferred embodiments, the formed peroxyhydroxycarboxylic acids have a vapor pressure below about 1 KPa, 0.5 KPa, 0.1 KPa, or 0.01 KPa.

TABLE 1

Physical Property of Exemplary Alphacarboxylic Acids and Peroxyalphacarboxylic Acids

| Compound | Vapor Pressure (20° C.) (KPa) | Odor |
| --- | --- | --- |
| Acetic Acid | 1.56 | Sour |
| Peracetic acid | 2.06 | Sharp pungent |
| Lactic Acid | 0.01 | No irritative odor |
| Peroxylactic acid | NA | Odorless |
| Glycolic acid | 0.003 | Odorless |
| Peroxyglycolic acid | NA | Odorless |

Any suitable lactone precursor of the alphahdroxycarboxylic acid can be used in the present methods. In embodiments, the lactone precursor is a diester of lactone. A lactone refers to a cyclic carboxylic ester containing a (—C=O)—O—) structure, and a diester of lactone has two carboxylic ester groups, such as shown in the following general structure:

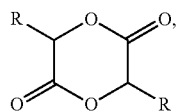

wherein R is H, $CH_3$ or an alkyl group. In preferred embodiments, the R is H or $CH_3$. In further embodiments, the lactone of the alphahdroxycarboxylic acid is lactide or glycolide. In embodiments the lactide or glycolide reagents are provided as powders or solids and/or may be provided in suitable solvents in a liquid form.

Any suitable hydrogen peroxide or peroxide generating substance can be employed as a reagent. Substances that generate hydrogen peroxide when in contact with a liquid include for example, sodium percarbonate, sodium perborate, calcium peroxide, magnesium peroxide, PVP peroxide and urea peroxide. In embodiments the hydrogen peroxide is available as a liquid, and the peroxide generating substance is provided as a powder or other solid form.

Any suitable alkalinity source can be employed as a reagent that increases the pH of the reaction conditions. Suitable sources of alkalinity can include, but is not limited to, an alkaline metal hydroxide, an alkaline earth metal hydroxide, an alkali metal silicate, an alkali metal carbonate, borates, amines, amides or other basic nitrogen sources and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. Suitable amines include, but are not limited to, primary, secondary or tertiary amines and diamines carrying at least one nitrogen linked hydrocarbon group, which represents a saturated or unsaturated linear or branched alkyl group having at least 1 carbon atom. Amines may further include alkanolamines including, for example, monoethanolamine, monoisopropanolamine, diethanolamine, diisopropanolamine, triethanolamine, triisopropanolamine and the like.

In preferred embodiments, the alkalinity source is an alkaline metal hydroxide, an alkaline earth metal hydroxide, or an alkali metal carbonate. In further preferred embodiments, the alkalinity source is an alkaline metal hydroxide or an alkaline earth metal hydroxide.

Methods of Making Peroxyhydroxycarboxylic Acids

Peroxyhydroxycarboxylic acids are formed through perhydrolysis of corresponding lactone precursors according to the methods described herein. The methods include the step of contacting reagents comprising a lactone of an alphahydroxycarboxylic acid, an alkalinity source (e.g. hydroxide alkalinity source) and hydrogen peroxide or a substance that generates hydrogen peroxide when in contact with a liquid, to form a liquid that comprises the peroxyhydroxycarboxylic acid. In embodiments, the methods include the step of contacting a first reagent that comprises a lactone of an alphahdroxycarboxylic acid with a second reagent that comprises an alkalinity source and a third reagent that comprises hydrogen peroxide or a substance that generates hydrogen peroxide when in contact with a liquid, to form a liquid that comprises the peroxyhydroxycarboxylic acid.

Beneficially, the lactone of alphahydroxycarboxylic acids, such as lactide and glycolide are used as raw material to efficiently generate the corresponding peroxyalphahydroxycarboxylic acids through perhydrolysis with hydrogen peroxide (or a substance that generates hydrogen peroxide) in a stoichiometric reaction. The stoichiometric reaction employing one mole of lactone will generate one mole of the corresponding peroxyalphahydroxycarboxylic acid and one mole of the alphahydroxycarboxylic acid.

The methods for forming peroxyhydroxycarboxylic acid comprises contacting the reagents at a pH that is approximately neutral (such as above or equal to about pH 7) to alkaline providing mild reaction conditions compared to prior reactions for generating peroxycarboxylic acid compositions. In embodiments, the methods for forming peroxyhydroxycarboxylic acid comprises contacting the reagents at a pH of at least about 7 or greater. In embodiments, the methods for forming peroxyhydroxycarboxylic acid comprises contacting the reagents at a pH of about 7-12, about 7-11, about 7-10, about 8-12, about 8-11, or about 8-10 (or any range therein). In preferred embodiments, mild alkaline conditions for the forming peroxyhydroxycarboxylic acid comprises contacting the reagents at a pH of about 7-11 (or any range therein).

The methods for forming peroxyhydroxycarboxylic acid are quick reactions as they begin to generate peroxyhydroxycarboxylic acid nearly instantaneously under the mild conditions. In an embodiment, the methods generate the peroxyhydroxycarboxylic acid in a liquid solution comprising peroxyhydroxycarboxylic acid in concentrations from about 0.1 ppm to about 100,000 ppm, from about 0.1 ppm to about 90,000 ppm, from about 0.1 ppm to about 80,000 ppm, from about 0.1 ppm to about 70,000 ppm, from about 0.1 ppm to about 60,000 ppm, from about 0.1 ppm to about 50,000 ppm, from about 0.1 ppm to about 40,000 ppm, from about 0.1 ppm to about 30,000 ppm, from about 0.1 ppm to about 20,000 ppm, or from about 0.1 ppm to about 10,000 ppm.

The present methods can be used to form a liquid, e.g., a solution that comprises any suitable concentration of the peroxyhydroxycarboxylic acid within any suitable time. For example, the reagents can be contacted with each other to form a liquid, e.g., a solution, that comprises any suitable concentration of the peroxyhydroxycarboxylic acid, such as at least about 1 ppm peroxyhydroxycarboxylic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, 5,000 ppm, 6,000 ppm, 7,000 ppm, 8,000 ppm, 9,000 ppm, 10,000 ppm, 20,000 ppm, 30,000 ppm, 40,000 ppm, 50,000 ppm, 60,000 ppm, 70,000 ppm, 80,000 ppm, 90,000 ppm, or 100,000 ppm (or ranges therebetween) within 1 minute of the contact time.

In an aspect, at least about 1 ppm peroxyhydroxycarboxylic acid is generated within less than 1 minute of contacting the reagents. In an aspect, at least about 1 ppm peroxyhydroxycarboxylic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyhydroxycarboxylic acid is near instantaneous. Beneficially, the use of the diester lactone of alphahydroxycarboxylic acids to generate the peroxyhydroxycarboxylic acids provides a near instantaneous reaction, which is distinct from reacting with monoester precursors or the corresponding hydroxycarboxylic acids.

In an aspect, at least about 100 ppm, at least about 500 ppm, at least about 1,000 ppm, at least about 10,000 ppm, or at least about 20,000 ppm peroxyhydroxycarboxylic acid is generated within about 5 minutes or less, about 3 minutes to about 5 minutes, or about 3 minutes or less of contacting the reagents. In an aspect, at least about 100 ppm, at least about 500 ppm, at least about 1,000 ppm, at least about 10,000 ppm, or at least about 20,000 ppm peroxyhydroxycarboxylic acid is generated within less than about 4 minutes, 3 minutes or less, 2 minutes or less, or 1 minute or less.

As the methods for forming peroxyhydroxycarboxylic acid are quick reactions they begin to generate peroxyhydroxycarboxylic acid as well as decrease the pH nearly instantaneously under the mild conditions. In an embodiment, the methods generate the peroxyhydroxycarboxylic acid and decrease the pH of the peroxyhydroxycarboxylic acid composition to below about 7, or below about 6 within about 1 minute, about 2 minutes, or about 3 minutes after the contact between the reagents.

In some embodiments, the pH of the formed peroxyhydroxycarboxylic acid liquid can become about 7 or lower, or 6 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the reagents. In other embodiments, the pH of the formed peroxyhydroxycarboxylic acid liquid can become about lower than about 7, 6, 5, 4, 3, or 2 within about 1 minute, about 2 minutes, or about 3 minutes after the contact between the reagents. In an aspect, the pH of the formed peroxyhydroxycarboxylic acid liquid becomes about 7 or lower, about 6 or lower within about 1 minute or less. In an aspect, the pH of the formed peroxyhydroxycarboxylic acid liquid becomes about 7 or lower, about 6 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed peroxyhydroxycarboxylic acid liquid becomes about 7 or lower, or about 6 or lower near instantaneously.

In embodiments the formed peroxyhydroxycarboxylic acid liquid maintains a pH lower than about 7, 6, 5, 4, 3, or 2 from about 1 second to about 10 hours after generation from the contacting of the reagents. In other embodiments, the formed peroxyhydroxycarboxylic acid liquid maintains the pH lower than about 7, 6, 5, 4, 3, or 2 from about 60 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

The reagents can be contacted with each other to form a liquid, e.g., a solution, that comprises the peroxyhydroxycarboxylic acid under any suitable conditions or temperature. In some embodiments, the reagents are contacted with each other under ambient conditions. In other embodiments, the reagents are contacted with each other at a temperature ranging from about −2° C. to about 60° C., 0° C. to about 60° C., or preferably about 4° C. to about 60° C., e.g., about −2° C.-0° C., 0° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C.

The methods can further comprise using a catalyst or an enzyme that catalyzes formation of the peroxyhydroxycarboxylic acid from the lactone precursor of the alphahdroxycarboxylic acid and hydrogen peroxide. The present methods can use any suitable catalyst or enzyme, e.g., a perhydrolytic enzyme, lipase, coronase, termanyl or esperase. The catalyst or an enzyme can be comprised in any suitable reagent.

In some embodiments, the methods do not comprise using a perhydrolysis enzyme. For example, in some cases, the present methods do not comprise using a member of family 7 of the carbohydrate esterases (CE-7) or a perhydrolysis enzyme that is disclosed in U.S. Pat. No. 8,865,436.

Beneficially, the methods do not require use of a stabilizing agent for the peroxyhydroxycarboxylic acid, a stabilizing agent for hydrogen peroxide, and/or a pH buffering agent. However, in other embodiments one or more stabilizing agents can be employed. As referred to herein, stabilizing agents include phosphonate based stabilizers including phosphonate salt(s), phosphoric acid and salts, pyrophosphoric acid and salts and most commonly 1-hydroxyethylidene-1,1-diphosphonic acid (HEDP) and salts, pyridine carboxylic acids, and/or a heterocyclic dicarboxylic acid, e.g., dipicolinic acid, picolinic acid and salts, pyridine-2,6-dicarboxylic acid and salts. Commonly used stabilizing agents in peroxycarboxylic acid compositions include HEDP and 2,6-pyridinedicarboxylic acid (DPA).

In embodiments where the methods use a pH buffering agent, these can include any reagent that is compatible with the lactone precursors. Exemplary buffer agents include an organic amine, such as triethanol amine, imidazole, carbonate salts, phosphate salts, etc.

The present methods can use any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable reagent.

The methods can use any suitable number of dosage(s) of the reagent comprising the lactone of an alphahydroxycarboxylic acid precursor to the other reagents during the methods of generation. In an embodiment the reagent comprising the lactone of an alphahdroxycarboxylic acid precursor is kept separately prior to use, and is used to contact the other reagents, namely the hydrogen peroxide or substance that generates hydrogen peroxide and the alkalinity source. In an embodiment, the methods can use a single dosage of the lactone precursor reagent that is kept separately prior to use, and is used to contact the remaining reagents. In another embodiment, the methods can use multiple dosages of the lactone precursor reagent during the contacting step. The multiple dosages of the lactone precursor reagent can comprise the same lactone precursor. In another embodiment, the multiple dosages of the lactone precursor reagent can comprise different lactone precursors of alphahdroxycarboxylic acids. The multiple dosages of the lactone precursor reagent can comprise the same or different concentrations of lactone precursor.

As the methods can use any suitable concentration of the precursors, the methods can employ any suitable concentration of the lactone of an alphahdroxycarboxylic acid precursor. For example, the lactone of an alphahdroxycarboxylic acid reagent of the peroxyhydroxycarboxylic acid forming composition can comprise any suitable concentration, such as up to about 90 wt-% of the reagents of the peroxyhydroxycarboxylic acid forming composition. In some embodiments, the amount of the lactone of an alphahdroxycarboxylic acid reagent in the formed liquid to generate the peroxyhydroxycarboxylic acid can comprise from about 1 ppm to about 500,000 ppm, or from about 10 ppm to about 500,000 ppm. For example, the lactone of an alphahdroxycarboxylic acid reagent in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm (and any other ranges there between).

As the methods can use any suitable concentration of the precursors, the methods can employ any suitable concentration of the hydrogen peroxide or a substance that generates hydrogen peroxide upon contact with a liquid. For example, the hydrogen peroxide or a substance that generates hydrogen peroxide upon contact with a liquid, can comprise any suitable concentration, such as up to about 10 wt-% of the reagents of the peroxyhydroxycarboxylic acid forming composition. In some embodiments, the amount of the hydrogen peroxide or a substance that generates hydrogen peroxide upon contact with a liquid can comprise from about 0.1 ppm to about 100,000 ppm, or from about 1 ppm to about 100,000 ppm. For example, the hydrogen peroxide or a substance that generates hydrogen peroxide upon contact with a liquid reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm hydrogen peroxide (and any other ranges there between).

As the methods can use any suitable concentration of the precursors, the methods can employ any suitable concentration of the alkalinity source. For example, the alkalinity source can comprise any suitable concentration to provide the reaction pH condition desired, such as up to about 10 wt-% of the reagents of the peroxyalphahydroxycarboxylic acid forming composition. In some embodiments, the amount of the alkalinity source can comprise from about 0.1 ppm to about 100,000 ppm, or from about 1 ppm to about 100,000 ppm. For example, the alkalinity source reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm alkalinity source (and any other ranges there between).

The methods can be used to generate the peroxyhydroxycarboxylic acid in any suitable manner or at any suitable location. In some embodiments, the methods can be used to generate peroxyhydroxycarboxylic acid in situ for the application of the formed peroxyhydroxycarboxylic acid.

Beneficially, the methods for forming peroxyhydroxycarboxylic acids can include comprises contacting the reagents which are in the form of powders and/or liquids. In embodiments, all reagents can be provided as powders (and combined as a premix) and can be combined with water at the point of contacting the reactants. In other embodiments, one or more reagents can be provided as powders (and combined as a premix) and can be combined with the remaining reagents and/or water at the point of contacting. In some embodiments a solvent is employed to disperse a powder reagent, such as the lactone precursor reagent, into a liquid. Exemplary solvents can include food grade solvents, including but not limited to propylene glycol, glycerol, ethanol or mixtures thereof.

In an exemplary embodiment, a solid material premix (e.g. lactide and percarbonate) can be applied directly to a surface and/or target in need of treatment (e.g. disinfection, sanitizing, bleaching or the like) and a liquid can then be applied from a separate premix, such as containing water, alkalinity and/or peroxide. In such an embodiment, the peroxyhydroxycarboxylic acid is generated directly on the surface and/or target in need of treatment.

In an embodiment, any reagents in the form of a powder are combined into a single composition prior to the contacting. In an embodiment, any reagents in the form of a liquid are kept separately prior to the contacting to generate the peroxyhydroxycarboxylic acid. In a further embodiment, the lactone of the alphahdroxycarboxylic acid and the hydrogen peroxide or a substance that generates hydrogen peroxide are kept separately prior to said contacting. In a still further embodiment, the lactone of the alphahdroxycarboxylic acid and the alkalinity source are kept separately prior to said contacting. In a still further embodiment, the hydrogen peroxide or a substance that generates hydrogen peroxide and the alkalinity source are kept separately prior to said contacting.

The peroxyhydroxycarboxylic acids and/or the peroxyhydroxycarboxylic acid forming compositions can further comprise additional peroxycarboxylic acids. Various embodiments referring to the peroxyhydroxycarboxylic acids or/or peroxyhydroxycarboxylic acid forming compositions are further understood to optionally comprise additional peroxycarboxylic acids. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

In some embodiments, the peroxyhydroxycarboxylic acid with additional peroxycarboxylic acids can be generated by mixing an ester of a polyhydric alcohol with a composition comprising peroxycarboxylic acid(s) and hydrogen peroxide to form a composition that comprises both the peroxyhydroxycarboxylic acid (e.g. peroxylactic acid and/or peroxyglycolic acid) and other peroxycarboxylic acid(s). Examples of compositions comprising both peroxycarboxylic acid and hydrogen peroxide include peroxyacetic acid compositions, peroxyoctanoic acid compositions, etc., all are commercially available from Ecolab Inc. In an embodiment, the reagents described herein including the lactone of an alphahdroxycarboxylic acid can be contacted, e.g., mixed, with Oxonia Active, Tsunami 100, Matrixx, TurboOxysan and Octave, etc., to form a composition that comprises both the peroxyhydroxycarboxylic acid and other desired peroxycarboxylic acid(s).

Peracids suitable for use include any peroxycarboxylic acids, including varying lengths of peroxycarboxylic and percarboxylic acids (e.g. C1-22) that can be prepared from the reaction of an ester of a polyhydric alcohol and acid with hydrogen peroxide as described herein. Additional suitable peracids include those of acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. Pat. Nos. 8,846,107 and 8,877,254 each titled "In Situ Generation of Peroxycarboxylic Acids at Alkaline pH, and Methods of Use Thereof," which are incorporated herein by reference. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference.

In another embodiment, a sulfoperoxycarboxylic acid has the following formula:

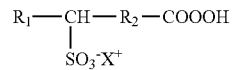

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof.

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. In additional embodiments, the compositions include the peroxyhydroxycarboxylic acid, peroxyacetic acid and/or peroxyoctanoic acid. Other combinations of mixed peracids are well suited for use in the methods and compositions described herein.

In some applications of use, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a mixture of the peroxyhydroxycarboxylic acid and one or more additional peroxycarboxylic acids.

Depending upon a particular application of use, any suitable $C_1$-$C_{22}$ percarboxylic acid can be used. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid.

The additional $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. In yet other embodiments, the $C_1$-$C_{22}$ percarboxylic acid has a concentration from about 0.1 ppm to about 10,000 ppm, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm.

Additional Optional Ingredients for Methods and/or Reagents

The peroxyhydroxycarboxylic acid compositions or peroxyhydroxycarboxylic acid forming compositions can optionally include additional ingredients to enhance the composition for treating various surfaces and targets. Additional optional functional ingredients may include for example, stabilizers, emulsifiers, surfactants and/or additional antimicrobial agents for enhanced efficacy (e.g. mixed peracids, biocides), antifoaming agents, anti-redeposition agents, bleaching agents, dispersants, solubility modifiers, wetting agents, metal protecting agents, sequestrants and/or chelating agents, fragrances and/or dyes, rheology modifiers, hydrotropes or couplers, buffers, solvents, acidulants and/or catalysts (e.g. strong mineral acids), additional carboxylic acids, and the like. In an embodiment, no additional functional ingredients are employed.

Additional Antimicrobial Agents

Additional antimicrobial agents may be included in the compositions (either the peroxyhydroxycarboxylic acid compositions or peroxyhydroxycarboxylic acid forming compositions) and/or methods of use for enhanced antimicrobial efficacy. In addition to the use of peroxyhydroxycarboxylic acid compositions, additional antimicrobial agents and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In some embodiments, additional antimicrobial and biocide agents may be employed in amounts sufficient to provide antimicrobial efficacy, as may vary depending upon the application of use. Such agents may be present in a use solution in an amount of at least about 0.1 wt-% to about 5 wt-%, preferably at least about 0.1 wt-% to about 2 wt-%, more preferably from about 0.1 wt-% to about 1 wt-%.

Acidulants

Beneficially, acidulants are not required in the methods and/or compositions described herein. However, in certain embodiments where the peroxyhydroxycarboxylic acid is preferred at a pH such as below about 2.5 or below about 2, an acidulant is an efficient component to decrease the pH of a composition. Accordingly, in some embodiments, an acidulant may be included as additional functional ingredients in the compositions (either the peroxyhydroxycarboxylic acid compositions or peroxyhydroxycarboxylic acid forming compositions). In an aspect, a strong mineral acid such as nitric acid or sulfuric acid can be used. The combined use of a strong mineral acid with the peracid composition provides enhanced antimicrobial efficacy. In some embodiments, the present composition does not comprise a mineral acid or a strong mineral acid.

In an aspect, the acidulant is included with the hydrogen peroxide reagent. Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboxylic acids, picolinic acid, dipicolinic acid, and mixtures thereof.

Acidulants may be employed in amounts sufficient to provide the intended antimicrobial efficacy. Such agents may be present in a use solution in an amount of at least about 0.1 wt-% to about 10 wt-%, preferably at least about 0.1 wt-% to about 5 wt-%, more preferably from about 0.1 wt-% to about 1 wt-%.

Enzymes

In an aspect of the invention, an enzyme can be included in the peroxyhydroxycarboxylic acid forming composition, including for example a catalase or peroxidase enzyme can be used to catalyze the reaction of the peroxyhydroxycarboxylic acid and/or to reduce and/or eliminate the concentration of hydrogen peroxide in an antimicrobial peracid composition. The enzymes catalyze the decomposition of hydrogen peroxide to water and oxygen.

Various sources of catalase enzymes may be employed according to the invention, including: animal sources such as bovine catalase isolated from beef livers; fungal catalases isolated from fungi including *Penicillium chrysogenum*, *Penicillium notatum*, and *Aspergillus niger*; plant sources; bacterial sources such as *Staphylcoccus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400 L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents, such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%.

In an aspect of the invention, the enzymes are suitable for use and have a tolerance to a wide range of temperatures, including the temperatures ranges in water treatment applications which may range from about 0-80° C. A suitable catalase enzyme will maintain at least 50% of its activity under such storage and/or application temperatures for at least about 10 minutes, preferably for at least about 1 hour.

In an aspect of the invention, a catalase or peroxidase enzyme is present in a use solution of the peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Wetting Agents

In an aspect, a wetting agent is present in the composition (either the peroxyhydroxycarboxylic acid compositions or peroxyhydroxycarboxylic acid forming compositions) in sufficient amounts. Wetting agents function to increase the surface contact or penetration activity of the peroxyhydroxycarboxylic acid composition. Wetting agents which can be used include any of those constituents known within the art to raise the surface activity of the composition. In an exemplary aspect, the wetting agent is a sulfonic acid or salt thereof (e.g., dodecylbenzene sulfonic acid, sodium salt). In certain embodiments, the wetting agent is present in amounts from about 0.001 to about 10 wt-% wetting agent, about 0.01 to about 1 wt-% wetting agent, about 0.01 to about 0.5 wt-% wetting agent, or about 0.1 to about 0.5 wt-% wetting agent.

Stabilizing Agents

Beneficially, stabilizing agents are not required in the methods and/or compositions described herein. However, in certain embodiments the compositions (either the peroxyhydroxycarboxylic acid compositions or peroxyhydroxycarboxylic acid forming compositions) can further comprise a stabilizing agent for the peroxyhydroxycarboxylic acid and/or a stabilizing agent for hydrogen peroxide. In an aspect, the peroxyhydroxycarboxylic acid forming compositions can further comprise peroxide, and/or a pH buffering agent. The present peroxyhydroxycarboxylic acid forming compositions can comprise any suitable pH buffering agent stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxyhydroxycarboxylic acid forming compositions comprise two or more stabilizing agents, e.g., HEDP and 2,6-pyridinedicarboxylic acid (DPA). In an aspect the stabilizing agent (s) can be comprised in any suitable part of the present peroxyhydroxycarboxylic acid forming compositions.

In an aspect, the peroxyhydroxycarboxylic acid forming compositions can further comprise any suitable pH buffering agent. The pH buffer reagent can include any reagent that is compatible with the lactone precursor in the peroxyhydroxycarboxylic acid forming compositions. Exemplary buffer agents can be an organic amine, such as triethanol amine, imidazole, etc., or a carbonate salt, a phosphate salt, etc. The pH buffer reagent can be comprised in any suitable part of the present peroxyhydroxycarboxylic acid forming compositions. In some embodiments, the first reagent comprises a pH buffering agent. In other embodiments, the peroxyhydroxycarboxylic acid forming compositions can further comprise a third reagent that comprises a pH buffering agent. In still other embodiments, the solid composition comprises a pH buffering agent.

In an aspect, the peroxyhydroxycarboxylic acid forming compositions can further comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the peroxyhydroxycarboxylic acid forming compositions. In some embodiments, the second reagent comprises a stabilizing agent for hydrogen peroxide. In other embodiments, the peroxyhydroxycarboxylic acid forming compositions can further comprise a third reagent that comprises a stabilizing agent for hydrogen peroxide. In still other embodiments, the solid composition comprises a stabilizing agent for hydrogen peroxide.

Surfactants

In some aspects of the invention, the peroxyhydroxycarboxylic acid compositions or peroxyhydroxycarboxylic acid forming compositions can include at least one surfactant. Surfactants are preferably included to increase solubility of the peroxyhydroxycarboxylic acid or to maintain the pH of the composition. According to an embodiment, the surfactant is a hydrotrope coupler or solubilizer, which can be used to ensure that the composition remains phase stable and in a single highly active aqueous form. Such hydrotrope solubilizers or couplers can be used at concentrations that maintain phase stability but do not result in unwanted compositional interaction. Surfactants particularly suitable for use with the compositions of the present invention include, but are not limited to, nonionic surfactants, anionic surfactants, amphoteric surfactants and zwitterionic surfactants. Preferably, nonionic and/or anionic surfactants are employed with the peracid compositions of the invention. Exemplary surfactants that can be used are commercially available from a number of sources. For a discussion of surfactants, see Kirk-Othmer, Encyclopedia of Chemical Technology, Third Edition, volume 8, pages 900-912.

Peracids are known to be strong oxidation agents, and as a result many chemicals, including commonly used surfactants are not compatible with concentrated peracids for extended presence of peracids. While it is ideal to use surfactants along with peracids to deliver preferred performance, such as cleaning, wetting et al., there is very limited choice of surfactants that could be put in preformed peracid formulations that meet the minimum shelf life requirements for commercial use. For examples, nonionic surfactants will be degraded by peracids, and cationic surfactants with halogen counter anions will decompose peracids. Some anionic surfactants, namely non substituted alkyl sulfonates, such as linear alkylbenzensulfonate, liner alkylsulfonate are more compatible with peracids and maybe used in some peracids compositions, but these anionic surfactants may not deliver the desired performance owing to their unwanted properties, such as high foam, water hardness tolerance as well as regulation requirements. In contrast, for onsite generated peracid compositions such as disclosed in the present art, all surfactants described above could be coexist with the peracids, as the generated peracids are only stored for very limited time, and typically in hours at the most, and the reactions between the surfactants and the peracids are not significant.

In some embodiments, the compositions include from about 1 wt-% to about 80 wt-% of a surfactant. In other embodiments the compositions include from about 1 wt-% to about 50 wt-% of a surfactant, or from about 1 wt-% to about 10 wt-% of a surfactant. In further embodiments, the compositions or a use solution of the composition include about 10 ppm to about 10,000 ppm of a surfactant. In further embodiments, the compositions or a use solution of the composition include about 10 ppm to about 100 ppm of a surfactant. It is to be understood that all ranges and values between these ranges and values are encompassed by the present invention.

Nonionic Surfactants

Suitable nonionic surfactants suitable for use with the compositions include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates; and capped alcohol alkoxylates, such as Plurafac LF221; mixtures thereof, or the like.

Semi-Polar Nonionic Surfactants

The semi-polar type of nonionic surface active agents are another class of nonionic surfactant useful in compositions. Semi-polar nonionic surfactants include the amine oxides, phosphine oxides, sulfoxides and their alkoxylated derivatives.

Amine oxides are tertiary amine oxides corresponding to the general formula:

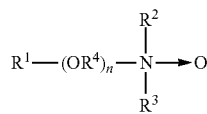

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl)amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside, and the like. Also included are the alkyl sulfates, alkyl poly(ethyleneoxy)ether sulfates and aromatic poly(ethyleneoxy)sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—$(CH_2CH_2O)_n(CH_2)_m$—$CO_2X$ in which R is a $C_8$ to $C_{22}$ alkyl group or

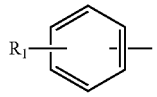

in which $R_1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

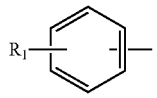

and $R_1$ is a $C_6$-$C_{12}$ alkyl group. In still yet other embodiments, $R_1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphate, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Exemplary suitable amphoteric surfactants include long chain imidazole derivatives, including carboxymethylated compounds (glycinates) which are frequently are called betaines. Betaines are a special class of amphoteric discussed herein below in the section entitled, Zwitterion Surfactants. These and other amphoteric surfactants are further described in U.S. patent application Ser. No. 12/568,493, entitled "Sulfoperoxycarboxylic Acids, Their Preparation and Methods of Use as Bleaching and Antimicrobial Agents," hereby expressly incorporated herein in its entirety by reference.

Long chain imidazole derivatives having application in the present invention generally have the general formula:

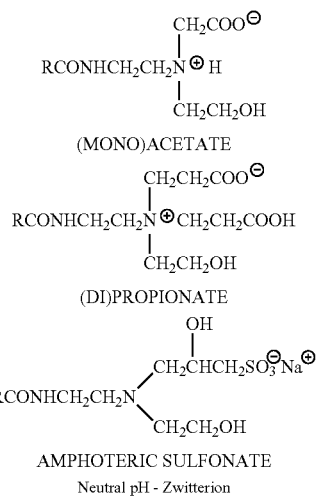

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Additionally suitable amphoteric surfactants include long chain N-alkylamino acids which are readily prepared by reaction $RNH_2$, in which R=$C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2- carboxyethyl)alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)$ 2-$CH_2$—$CH_2$—OH. Disodium cocoampho dipropionate is one suitable amphoteric surfactant and is commercially available under the tradename Miranol™ FBS from Rhodia Inc. (Cranbury, N.J). Another suitable coconut derived amphoteric surfactant with the chemical name disodium cocoampho diacetate is sold under the tradename Mirataine™ JCHA, also from Rhodia Inc.

A typical listing of amphoteric classes, and species of these surfactants, is given in U.S. Pat. No. 3,929,678 issued to Laughlin and Heuring on Dec. 30, 1975 and further examples are given in "Surface Active Agents and Detergents" (Vol. I and II by Schwartz, Perry and Berch), each of which are hereby expressly incorporated herein in its entirety by reference.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

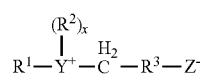

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

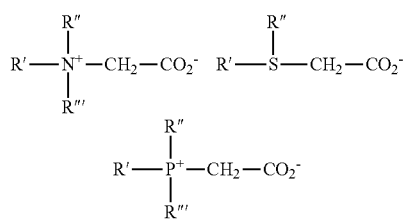

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically a $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Methods for Treating a Target with a Peroxyhydroxycarboxylic Acid

In an aspect, the methods of forming a peroxyhydroxycarboxylic acid composition and the peroxyhydroxycarboxylic acid compositions are suitable for use in treating a surface or a target, which method comprises contacting a surface or a target with an effective amount of peroxyhydroxycarboxylic acid formed using the above methods to form a treated surface or target composition, wherein said treated surface or target composition comprises from about 0.1 ppm to about 10,000 ppm of said peroxyhydroxycarboxylic acid acid, and said contacting step lasts for sufficient time to stabilize or reduce microbial population in and/or on said surface or target or said treated surface of target composition.

Beneficially, according to various embodiments, the methods of using the peroxyhydroxycarboxylic acid compositions do not require a stabilizer for the composition. In some embodiments, the compositions used comprises peroxyhydroxycarboxylic acid (e.g. perlactic acid), hydrogen peroxide, lactic acid and a solvent, e.g., water. In some embodiments, the composition used in the present methods does not comprise a mineral acid, e.g., the mineral acids disclosed in WO 91/07375.

The peroxyhydroxycarboxylic acid and the surface or target can be contacted to form a treated target composition comprising any suitable concentration of said peroxyhydroxycarboxylic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm of peroxyhydroxycarboxylic acid. In preferred embodiments, the peroxyhydroxycarboxylic acid and the surface or target can be contacted to form a treated target composition comprising from about 0.1-2,000 ppm, about 1-2,000 ppm, about 10-2,000 ppm, about 10-1,000 ppm, or about 100-1,000 ppm of said peroxyhydroxycarboxylic acid.

In some embodiments, the target to be treated by the present methods can be a food item or a plant item and/or at least a portion of a medium, a container, an equipment, a system or a facility for growing, holding, processing, packaging, storing, transporting, preparing, cooking or serving the food item or the plant item. Any suitable concentration of peroxyhydroxycarboxylic acid can be used in the present methods. For example, the peroxyhydroxycarboxylic acid can be used at a concentration from about 1 ppm to about 100 ppm, e.g., about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm of peroxyhydroxycarboxylic acid. In some embodiments, the target is a food item or a plant item and the contacting step minimizes or does not induce an organoleptic effect in and/or on the food item or a plant item.

The present methods can be used for treating any suitable plant item. In some embodiments, the plant item is a grain, fruit, vegetable or flower plant item. In other embodiments, the plant item is a living plant item or a harvested plant item. In still other embodiments, the plant item comprises a seed, a tuber, a growing plant, a cutting, or a root stock. In yet other embodiments, the present methods are used for treating a living plant tissue comprising treating the plant tissue with the above composition in a diluted concentration to stabilize or reduce microbial population in and/or on the plant tissue. In yet other embodiments, the present methods are used for growing a plant on a hydroponic substrate in a hydroponic liquid supply medium, comprising: (a) establishing a growing and living plant tissue in the hydroponic substrate; (b) contacting the living plant tissue, the hydroponic substrate and the hydroponic liquid with a composition of the present invention to stabilize or reduce microbial population in and/or on the living plant tissue; and (c) harvesting a usable plant product with reduced microbial contamination.

The present methods can be used for treating any suitable food item. For example, the food item can be an animal product, e.g., an animal carcass or an egg, a fruit item, a vegetable item, or a grain item. In some embodiments, the animal carcass can be a beef, pork, veal, buffalo, lamb, fish, sea food or poultry carcass. In other embodiments, the sea food carcass can be scallop, shrimp, crab, octopus, mussel, squid or lobster. In still other embodiments, the fruit item can be a botanic fruit, a culinary fruit, a simple fruit, an aggregate fruit, a multiple fruit, a berry, an accessory fruit or a seedless fruit. In yet other embodiments, the vegetable item can be a flower bud, a seed, a leaf, a leaf sheath, a bud, a stem, a stem of leaves, a stem shoot, a tuber, a whole-plant sprout, a root or a bulb. In yet other embodiments, the grain item can be maize, rice, wheat, barley, sorghum, millet, oat, triticale, rye, buckwheat, fonio or quinoa.

In some embodiments, the target to be treated by the present methods can be a medium, a surface, a container, an equipment, or a system in a health care facility, e.g., a physical office or a hospital. Any suitable concentration of peroxyhydroxycarboxylic acid can be used in the present methods. For example, the peroxyhydroxycarboxylic acid can be used at a concentration from about 10 ppm to about 300 ppm, e.g., 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, or 250-300 ppm of peroxyhydroxycarboxylic acid.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The peroxyhydroxycarboxylic acid can be applied in any suitable manner. In some embodiments, the peroxyhydroxycarboxylic acid can be applied to a target by means of a spray, a fog, or a foam, or by dipping all or part of the target in a composition comprising the peroxyhydroxycarboxylic acid. In some embodiments, the peroxyhydroxycarboxylic acid composition is applied to the target by means of a spray, a fog, or a foam. In other embodiments, the diluted peroxyhydroxycarboxylic acid is applied to the target by applying in the form of a thickened or gelled solution. In still other embodiments, all or part of the target is dipped in the peroxyhydroxycarboxylic acid composition. The target and/or the peroxyhydroxycarboxylic acid composition can be subject to any suitable movement to help or facilitate the contact between the target and the peroxyhydroxycarboxylic acid composition. In some embodiments, the peroxyhydroxycarboxylic acid composition can be agitated. In other embodiments, the peroxyhydroxycarboxylic acid composition can be sprayed onto a target, e.g., an animal carcass, under suitable pressure and at a suitable temperature. For example, the peroxyhydroxycarboxylic acid composition can be sprayed onto an animal carcass at a pressure of at least 50 psi at a temperature of up to about 60° C., resulting in a contact time of at least 30 seconds.

The present methods can comprise any suitable, additional steps. In some embodiments, the present methods can comprise a vacuum treatment step. In other embodiments, the present methods can comprise a step of applying an activated light source to the target, e.g., an animal carcass.

The contacting step in the present methods can last for any suitable amount of time. In some embodiments, the contacting step can last for at least about 1 second, or at least about 10 seconds. For example, the contacting step can last for at least about 10, 20, 30, 40, 50 seconds, 1 minute, 1-2 minutes, 2-3 minutes, 3-4 minutes, 4-5 minutes, 5-6 minutes, 6-7 minutes, 7-8 minutes, 8-9 minutes, or 9-10 minutes, 10-15 minutes, 15-20 minutes, 20-25 minutes, 25-30 minutes, 30-40 minutes, 40-50 minutes, 50-65 minutes, 1-2 hours, 2-3 hours, 3-4 hours, 4-5 hours, 5-6 hours, 6-7 hours, 7-8 hours, 8-9 hours, or 9-10 hours, 16 hours, 1 day, 3 days, 1 week, or longer. In an aspect, the contacting occurs for a period of time before degradation of the peroxyhydroxycarboxylic acid composition.

The present methods can be used to reduce microbial population in and/or on the target or the treated target composition by any suitable magnitude. In some embodiments, the present methods can be used to reduce microbial population in and/or on the target or the treated target composition by at least one $\log_{10}$, two $\log_{10}$, three $\log_{10}$, four $\log_{10}$, five $\log_{10}$, or more. In other embodiments, the level of a microorganism, if present in and/or on the target or the treated target composition, can be stabilized or reduced by the present methods. For example, at least 10%, 20%, 30%, 40%, 50%, 60%, 70%, 80%, or 90% or more of the microorganism, if present in and/or on the target or the treated target composition, can be killed, destroyed, removed and/or inactivated by the present methods.

The present methods can be used to reduce population of any suitable microbe(s) in and/or on the target or the treated target composition by any suitable magnitude. In some embodiments, the present methods can be used to reduce a prokaryotic microbial population, e.g., a bacterial or an archaeal population. In other embodiments, the present methods can be used to reduce a eukaryotic microbial population, e.g., a protozoal or fungal population. In still other embodiments, the present methods can be used to reduce a viral population. Exemplary viral population can comprise a population of a DNA virus, an RNA virus, and a reverse transcribing virus.

The present methods can be used to stabilize or reduce a microbial population in and/or on the target or the treated target composition, wherein the target is a food item or a plant item and the contacting step minimizes or does not induce an organoleptic effect in and/or on the food item or a plant item. Typical organoleptic properties include the aspects of food or other substances as experienced by the senses, including taste, sight, smell, and touch, in cases where dryness, moisture, and stale-fresh factors are to be considered. See e.g., Jasper Womach, the Congressional Research Service document "Report for Congress: Agriculture: A Glossary of Term, Programs, and Laws, 2005 Edition." In some embodiments, organoleptic procedures are performed as part of the meat and poultry inspections to detect signs of disease or contamination. In other embodiments, organoleptic tests are conducted to determine if package materials and components can transfer tastes and odors to the food or pharmaceutical products that they are packaged in. Shelf life studies often use taste, sight, and smell (in addition to food chemistry and toxicology tests) to determine whether a food product is suitable for consumption. In still other embodiments, organoleptic tests are conducted as part of the Hurdle technology. Typically, Hurdle technology refers to an intelligent combination of hurdles which secures the microbial safety and stability as well as the organoleptic and nutritional quality and the economic viability of food products. See generally, Leistner L (1995) "In Gould G W (Ed.) *New Methods of Food Preservation*, Springer, pp. 1-21; and Leistner I (2000)" *International Journal of Food Microbiology*, 55:181-186.

The present methods can be conducted at any suitable temperature range. In some embodiments, the present methods can be conducted at a temperature ranging from about 0° C. to about 70° C., e.g., about 0° C.-1° C., 1° C.-2° C., 2° C.-3° C., 3° C.-4° C., 4° C.-5° C., 5° C.- 10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted at a temperature at or lower than 0° C.

In some embodiments, the present methods can comprise adding a peroxidase or a catalase to further reduce the hydrogen peroxide level in and/or on the target or the treated target composition. The peroxidase or catalase can be added in any suitable manner. In some embodiments, the peroxidase or catalase can be added to the target or the treated target composition before a composition used in the present methods is provided to the target. In other embodiments, the present compositions can be diluted into a suitable intermediate volume, and the peroxidase or catalase can be added to the diluted, intermediate volume. Thereafter, the diluted, intermediate volume, which contains the peroxidase or catalase, can be added to target. Any suitable peroxidase or catalase, including the ones described below, can be used in the present methods.

Use in Water Treatment

The present methods can be used to treat any suitable surface or target. In some embodiments, the target is water, and the present methods can comprise providing an effective amount of peroxyhydroxycarboxylic acid formed using the above methods to a water source in need of treatment to form a treated water source, wherein said treated water source comprises from about 1 ppm to about 10,000 ppm of said peroxyhydroxycarboxylic acid, e.g., about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyhydroxycarboxylic acid.

The present methods can be used to treat any suitable water source. For example, a water source in need of treatment can be fresh water, pond water, sea water, produced water, paper manufacturing water, tower water or a combination thereof.

In some embodiments, the tower water is cooling water and the treated water source comprises from about 1 ppm to about 10 ppm of the peroxyhydroxycarboxylic acid, e.g., about 1-2 ppm, 2-3 ppm, 3-4 ppm, 4-5 ppm, 5-6 ppm, 6-7 ppm, 7-8 ppm, 8-9 ppm, or 9-10 ppm peroxyhydroxycarboxylic acid. The contacting step can last any suitable amount of time, e.g., about 1-2 minutes, 2-3 minutes, 3-4 minutes, 4-5 minutes, 5-6 minutes, 6-7 minutes, 7-8 minutes, 8-9 minutes, or 9-10 minutes. The contacting step can be conducted at suitable temperature range. For example, the contacting step can be conducted at a temperature ranging from about 0° C. to about 60° C., e.g., about 0° C.-1° C., 1° C.-2° C., 2° C.-3° C., 3° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C.

In some embodiments, the present methods can be used to treat a water source used in oil or gas drilling operation. For example, the present methods can be used to treat a water source used in an operation of induced hydraulic fracturing (hydrofracturing or fracking). The water source can comprise a friction reducer or a viscosity enhancer. The present methods can be used to treat a water source to form a treated water source that comprises from about 1 ppm to about 10 ppm of the peroxyhydroxycarboxylic acid, e.g., about 1-2 ppm, 2-3 ppm, 3-4 ppm, 4-5 ppm, 5-6 ppm, 6-7 ppm, 7-8 ppm, 8-9 ppm, or 9-10 ppm peroxyhydroxycarboxylic acid. The present methods can further comprise disposing of the treated water source. The present methods can further comprise directing the treated water source into a subterranean environment, e.g., a subterranean environment that comprises a well in a gas and/or oil. In some embodiments, the target water to be treated contains iron sulfide and/or H2S, and the present methods can be used to oxidize iron sulfide and/or reduce or eliminate H2S in the target water. In other embodiments, the target water to be treated needs to be clarified, e.g., containing particles, and the present methods can be used to clarify the target water.

In some embodiments, the target to be treated by the present methods can be water and/or at least a portion of a medium, a container, an equipment, a system or a facility for producing, holding, processing, packaging, storing, or transporting pulp. The present methods can be used to treat water and/or other target(s) for any suitable purpose. For example, the present methods can be used in papermaking, textiles, food, or pharmaceutical industry. The present methods can be used to treat a water source, alone or in combination with other target(s), to form a treated water source that comprises any suitable concentration of peroxyhydroxycarboxylic acid, e.g., about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm of peroxyhydroxycarboxylic acid.

The peroxyhydroxycarboxylic acid compositions can be used for a variety of industrial applications, e.g., to reduce microbial or viral populations on a surface or object or in a body or stream of water. In some aspects, the invention includes methods of using the peroxyhydroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, peroxyhydroxycarboxylic acid and catalase compositions are used to control the growth of microorganisms in water used in various oil and gas operations. In a further aspect, the compositions are suitable for incorporating into fracturing fluids to control or eliminate microorganisms.

As used herein for the methods of the invention, the peroxyhydroxycarboxylic acid compositions can employ a variety of peroxyhydroxycarboxylic acid compositions having a low to substantially no hydrogen peroxide concentration. These peroxyhydroxycarboxylic acid compositions include peroxyhydroxycarboxylic acid compositions with a catalase or peroxidase enzyme to reduce the hydrogen peroxide to peracid ratio and/or other reduced hydrogen peroxide peroxyhydroxycarboxylic acid compositions disclosed herein. In a preferred embodiment peroxyhydroxycarboxylic acid and catalase use solutions having reduced or substantially no hydrogen peroxide are introduced to a water source in need of treatment.

The methods by which the peroxyhydroxycarboxylic acid solutions are introduced into the aqueous fluids according to the invention are not critical. Introduction of the peroxyhydroxycarboxylic acid compositions may be carried out in a continuous or intermittent manner and will depend on the type of water being treated. In some embodiments, the peroxyhydroxycarboxylic acid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

In some embodiments, the water source treated by the present methods does not comprise reuse water, the treated water source comprises from about 10 ppm to about 20 ppm of the in situ formed peroxyhydroxycarboxylic acid and from about 1 ppm to about 2 ppm of hydrogen peroxide and the treated water source does not comprise a friction reducer and/or a rheology modifier.

In some aspects, the methods disclosed for water treatment in oil and gas recovery provide effective antimicrobial efficacy without deleterious interaction with functional agents, including for example friction reducers. In a further aspect, the methods for water treatment provide increased antimicrobial efficacy compared to the use of the antimicrobial peracids alone. In a still further aspect, the methods of use result in the disposal of cleaner water with low numbers of microorganisms. In yet a further aspect of the methods of the invention, the reduction and/or elimination of $H_2O_2$ from the peracid compositions minimizes the negative effects of the oxidant $H_2O_2$. Still further, the methods of the invention reduce the volume expansion within sealed systems used in oil and gas recovery methods, as a result of the reduction and/or elimination of $H_2O_2$ from the systems.

In an aspect, the peroxyhydroxycarboxylic acid solutions are added to waters in need of treatment prior to the drilling and fracking steps in order to restrict the introduction of microbes into the reservoir and to prevent the microbes from having a negative effect on the integrity of the fluids. The treatment of source waters (e.g. pond, lake, municipal, etc.) and/or produced waters is particularly well suited for use according to the invention.

The treated waters according to the invention can be used for both slick water fracturing (i.e. using frictions reducers) and/or gel fracturing (i.e. using viscosity enhancers), depending on the type of formation being fractured and the type of hydrocarbon expected to be produced. Use of a peroxyhydroxycarboxylic acid solution, including a catalase treated peroxyhydroxycarboxylic acid composition use solution having low to substantially no hydrogen peroxide, is suitable for both slick water fracturing and gel fracturing. In an aspect, pretreating the peroxyhydroxycarboxylic acid composition with catalase substantially removes the hydrogen peroxide with minimal to no impact on the fracturing fluids and the well itself. In an aspect, the peroxyhydroxycarboxylic acid composition pretreated with catalase allows the formation of gel suitable for gel fracturing, as opposed to untreated peroxyhydroxycarboxylic acid composition solutions that do not allow a gel to form under certain conditions. In a further aspect, the peroxyhydroxycarboxylic acid composition solutions are added to waters in need of treatment in the subterranean well formations (e.g. introduced through a bore hole in a subterranean formation). These methods provide additional control within the well formation suitable for reducing microbial populations already present within the down hole tubing in the well or within the reservoir itself.

In a still further aspect, the peroxyhydroxycarboxylic acid composition solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In an aspect, the water source in need of treatment may vary significantly. For example, the water source may be a freshwater source (e.g. pond water), salt water or brine source, brackish water source, recycled water source, or the like. In an aspect, wherein offshore well drilling operations are involved, seawater sources are often employed (e.g. saltwater or non-saltwater). Beneficially, the peroxyhydroxycarboxylic acid compositions, with or without catalase, of the invention are suitable for use with any types of water and provide effective antimicrobial efficiency with any of such water sources.

Large volumes of water are employed according to the invention as required in well fluid operations. As a result, in an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect, thousands to millions of gallons of water may be employed and the combination of produced water with fresh water sources provides significant economic and environmental advantages. In an aspect, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed.

According to embodiments of the invention, a sufficient amount of the peroxyhydroxycarboxylic acid composition, with or without catalase, is added to the aqueous water source in need of treatment to provide the desired peroxyhydroxycarboxylic acid concentration for antimicrobial efficacy. For example, a water source is dosed amounts of the peroxyhydroxycarboxylic acid and catalase use solution composition until a peroxyhydroxycarboxylic acid concentration within the water source is detected within the preferred concentration range (e.g. about 1 ppm to about 100 ppm peracid). In an aspect, it is preferred to have a microbial count of less than about 100,000 microbes/mL, more preferably less than about 10,000 microbes/mL, or more preferably less than about 1,000 microbes/mL.

The methods of use as described herein can vary in the temperature and pH conditions associated with use of the aqueous treatment fluids. For example, the aqueous treatment fluids may be subjected to varying ambient temperatures according to the applications of use disclosed herein, including ranging from about 0° C. to about 130° C. in the course of the treatment operations. Preferably, the temperature range is between about 5° C. to about 100° C., more preferably between about 10° C. to about 80° C. However, as a majority of the antimicrobial activity of the compositions of the invention occurs over a short period of time, the exposure of the compositions to relatively high temperatures is not a substantial concern. In addition, the peracid composition aqueous treatment fluids (i.e. use solutions) may be subjected to varying pH ranges, such as from 1 to about 10.5.

The antimicrobial compositions of the invention are fast-acting. However, the present methods require a certain minimal contact time of the compositions with the water in need of treatment for occurrence of sufficient antimicrobial effect. The contact time can vary with concentration of the use compositions, method of applying the use compositions, temperature of the use compositions, pH of the use compositions, amount of water to be treated, amount of soil or substrates in the water to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. The contact time will further vary based upon the concentration of peracid in a use solution.

Beneficial Effects of the Methods of Use in Water Treatment

In an aspect, the methods of use provide an antimicrobial for use that does not negatively impact the environment. Beneficially, the degradation of the compositions of the invention provides a "green" alternative.

In a further aspect, the methods of use provide an antimicrobial for use that does not negatively interfere with friction reducers, viscosity enhancers and/or other functional ingredients. In a further aspect, the methods of use do not negatively interfere with any additional functional agents utilized in the water treatment methods, including for example, corrosion inhibitors, descaling agents and the like. The compositions administered according to the invention provide extremely effective control of microorganisms without adversely affecting the functional properties of any additive polymers of an aqueous system. In addition, the peroxyhydroxycarboxylic acid compositions provide additional benefits to a system, including for example, reducing corrosion within the system due to the decreased or substantially eliminated hydrogen peroxide from a treated composition. Beneficially, the non-deleterious effects of the peroxyhydroxycarboxylic acid compositions (with or without a catalase) on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In further aspects, the methods of use employ the antimicrobial and/or bleaching activity of the peroxyhydroxycarboxylic acid compositions. For example, the invention includes a method for reducing a microbial population and/or a method for bleaching. These methods can operate on an article, surface, in a body or stream of water or a gas, or the like, by contacting the article, surface, body, or stream with the compositions. Contacting can include any of numerous methods for applying the compositions, including, but not limited to, providing the antimicrobial peroxyhydroxycarboxylic acid compositions in an aqueous use solution and immersing any articles, and/or providing to a water source in need of treatment.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peroxyhydroxycarboxylic acid compositions of the invention include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum,* and *Aureobasidium pullulans*), filamentous fungi (e.g., *Aspergillus niger* and *Cladosporium resinae*), algae (e.g., *Chlorella vulgaris, Euglena gracilis,* and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449 A1, e.g., the sulfur- or sulfate-reducing bacteria, such as *Desulfovibrio* and *Desulfotomaculum* species.

Use in Other Treatments

Additional embodiments include water treatments for various industrial processes for treating liquid systems. As used herein, "liquid system" refers to flood waters or an environment within at least one artificial artifact, containing a substantial amount of liquid that is capable of undergoing biological fouling. Liquid systems include but are not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In a further aspect, the present methods can also be used to treat other liquid systems where both the compositions' antimicrobial function and oxidant properties can be utilized. Aside from the microbial issues surrounding wastewater, wastewater is often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

The present methods can be conducted at any suitable temperature. In some embodiments, the present methods are conducted at a temperature ranging from about $-2°$ C. to about $70°$ C., e.g., from about $0°$ C. to about $4°$ C. or $5°$ C., from about $5°$ C. to about $10°$ C., from about $11°$ C. to about $20°$ C., from about $21°$ C. to about $30°$ C., from about $31°$ C. to about $40°$ C., including at about $37°$ C., from about $41°$ C. to about $50°$ C., from about $51°$ C. to about $60°$ C., or from about $61°$ C. to about $70°$ C.

The present methods can be used in the methods, processes or procedures described and/or claimed in U.S. Pat. Nos. 5,200,189, 5,314,687 and 5,718,910. In some embodiments, the present methods can be used of sanitizing facilities or equipment comprises the steps of contacting the facilities or equipment with the composition of the present invention at a temperature in the range of about $4°$ C. to about $60°$ C. The peroxyhydroxycarboxylic acid composition is then circulated or left in contact with the facilities or equipment for a time sufficient to sanitize (generally at least 30 seconds) and the treated target composition is thereafter drained or removed from the facilities or equipment.

As noted above, the present methods are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) can be accomplished with a different material such as a formulated detergent which is introduced with heated water. After this cleaning step, the peroxyhydroxycarboxylic acid composition can be applied or introduced into the system at a use solution concentration in unheated, ambient temperature water. In some embodiments, the peroxyhydroxycarboxylic acid composition is found to remain in solution in cold (e.g., $40°$ F./$4°$ C.) water and heated (e.g., $140°$ F./$60°$ C.) water. Although it is not normally necessary to heat the aqueous use solution of the peroxyhydroxycarboxylic acid composition, under some circumstances heating may be desirable to further enhance its antimicrobial activity.

In some embodiments, a method of sanitizing substantially fixed in-place process facilities comprises the following steps. The peroxyhydroxycarboxylic acid composition of the present invention is introduced into the process facilities at a temperature in the range of about 4° C. to about 60° C. After introduction of the use solution, the solution is circulated throughout the system for a time sufficient to sanitize the process facilities (i.e., to kill undesirable microorganisms). After the system has been sanitized by means of the present composition, the use composition or solution is drained from the system. Upon completion of the sanitizing step, the system optionally may be rinsed with other materials such as potable water. The present composition is preferably circulated through the process facilities for 10 minutes or less.

In other embodiments, the present peroxyhydroxycarboxylic acid composition may also be employed by dipping food processing equipment into the diluted (or use) composition or solution of the present invention, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing the excess composition or solution by wiping, draining vertically, vacuuming, etc.

In still other embodiments, the present peroxyhydroxycarboxylic acid composition may also be used in a method of sanitizing hard surfaces such as institutional type equipment, utensils, dishes, health care equipment or tools, and other hard surfaces. The peroxyhydroxycarboxylic acid composition may also be employed in sanitizing clothing items or fabric which has become contaminated. The peroxyhydroxycarboxylic acid composition is contacted with any of the above contaminated surfaces or items at use temperatures in the range of about 4° C. to about 60° C. for a period of time effective to sanitize, disinfect, or sterilize the surface or item.

The present methods can be used in the methods, processes or procedures described and/or claimed in U.S. Pat. Nos. 6,165,483 and 6,238,685B1, to treat field or greenhouse grown plant tissue, seeds, fruits, and growing media and containers. The present peroxyhydroxycarboxylic acid composition can lower the natural, plant pathogen and human pathogenic microbial load resulting in less waste to molding, spoilage, and destruction because of pathogenic poisons.

In some embodiments, the present peroxyhydroxycarboxylic acid composition can be used to protect growing plant tissue from the undesirable effects of microbial attack. The peroxyhydroxycarboxylic acid composition can be applied to growing plant tissues and can provide residual antimicrobial effects after the plant has completed its growth cycle, fruit or vegetable material have been harvested and sent to market. The present composition can be an effective treatment of living or growing plant tissues including seeds, roots, tubers, seedlings, cuttings, rooting stock, growing plants, produce, fruits and vegetables, etc. Under certain circumstances, a single peroxyacid material can be effective, however, in other circumstances, a mixed peroxy acid has substantially improved and surprising properties.

Methods of Treating Animal/Protein Carcasses

The present methods can be used in the methods, processes or procedures described and/or claimed in U.S. Pat. Nos. 6,010,729, 6,103,286, 6,545,047 and 8,030,351 for sanitizing animal carcasses. In some embodiments, the compositions of the present invention can be used in a method of treating animal carcasses to obtain a reduction by at least 50%, 90%, 99%, or 99.9% or greater in surface microbial population which method includes the step of treating said carcass with a composition of the present invention comprising an effective antimicrobial amount comprising at least 1 parts per million (ppm, parts by weight per each one million parts) of one or more peroxyalphahydroxycarboxylic acids to reduce the microbial population.

In yet other embodiments, the present invention is directed to a method of treating an animal carcass to reduce a microbial population in resulting cut meat, the method comprising the steps of spraying an aqueous antimicrobial treatment composition onto said carcass at a pressure of at least 50 psi at a temperature of up to about 60° C. resulting in a contact time of at least 5 seconds, the antimicrobial composition comprising an effective antimicrobial amount comprising least 1 ppm of one or more carboxylic acid, peroxycarboxylic acid or mixtures thereof, and the first and second stabilizing agents described above; and achieving at least a one $\log_{10}$ reduction in the microbial population. Methods of use in both high and low temperature treatment of animal carcasses can be employed.

In yet other embodiments, the present invention is directed to a method of treating an animal carcass to reduce a microbial population in resulting cut meat, the method comprising the steps of placing the animal carcass in a chamber at atmospheric pressure; filling the chamber with condensing steam comprising an antimicrobial composition, e.g., a diluted composition of the present invention, for a short duration; and quickly venting and cooling the chamber to prevent browning of the meat carcass; wherein the duration of the steam thermal process may be from about 5 seconds to about 30 seconds and the chamber temperature may reach from about 50° C. to about 93° C.

The antimicrobial composition can be applied in various ways to obtain intimate contact with each potential place of microbial contamination. For example, it can be sprayed on the carcasses, or the carcasses can be immersed in the composition. Additional methods include applying a foamed composition and a thickened or gelled composition. Methods of use in treating microbial contamination on carcasses can be applied in both high and low temperatures. Vacuum and or light treatments can be included, if desired, with the application of the antimicrobial composition. Thermal treatment can also be applied, either pre-, concurrent with or post application of the antimicrobial composition.

One preferred spray method for treating carcasses with diluted compositions of the present invention involves spraying the carcass with an aqueous spray at a temperature less than about 60° C. at a pressure of about 50 to 500 psi gauge wherein the spray comprises an effective antimicrobial amount of a carboxylic acid, an effective antimicrobial amount of a peroxycarboxylic acid or mixtures thereof, and the first and second stabilizing agents described above. These sprays can also contain an effective portion of a peroxy compound such as hydrogen peroxide and other ingredients such as sequestering agents, etc. The high pressure spray action of the aqueous treatment can remove microbial populations by combining the mechanical action of the spray with the chemical action of the antimicrobial materials to result in an improved reduction of such populations on the surface of the carcass.

All pressures are psig (or psi gauge). In some embodiments, differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may affect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and may achieve at least a five-fold reduction (i.e., a five log 10 reduction) in microbial populations after a 30 second contact time (see AOAC method 960.09).

Methods of Industrial Applications

The present methods can be used in the methods, processes or procedures described and/or claimed in U.S. Pat. Nos. 8,017,409 and 8,236,573. In some embodiments, the present methods may be used for a variety of domestic or industrial applications, e.g., to reduce microbial or viral populations on a surface or object or in a body or stream of water. The peroxyhydroxycarboxylic acid compositions of the present invention may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or non-woven fabric, soft plastics and elastomers. The diluted (or use) compositions may also be applied to soft surfaces such as food and skin (e.g., a hand). The diluted (or use) compositions may be employed as a foaming or non-foaming environmental sanitizer or disinfectant.

In other embodiments, the peroxyhydroxycarboxylic acid compositions of the present invention may be included in products such as sterilants, sanitizers, disinfectants, preservatives, deodorizers, antiseptics, fungicides, germicides, yeasticidal, sporicides, virucides, detergents, bleaches, hard surface cleaners, hand soaps, waterless hand sanitizers, and pre- or post-surgical scrubs.

In still other embodiments, the peroxyhydroxycarboxylic acid compositions of the present invention may also be used in veterinary products such as mammalian skin treatments or in products for sanitizing or disinfecting animal enclosures, pens, watering stations, and veterinary treatment areas such as inspection tables and operation rooms. The peroxyhydroxycarboxylic acid compositions may be employed in an antimicrobial foot bath for livestock or people.

In yet other embodiments, the present methods may be employed for reducing the population of pathogenic microorganisms, such as pathogens of humans, animals, and the like. Exemplary pathogenic microorganisms include fungi, molds, bacteria, spores, and viruses, for example, *S. aureus, E. coli*, Streptococci, *Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The present methods may be used to reduce the population of microorganisms on skin or other external or mucosal surfaces of an animal. In addition, the present methods may be used to kill pathogenic microorganisms that spread through transfer by water, air, or a surface substrate. In some applications, the compositions of the present invention need only be applied to the skin, other external or mucosal surfaces of an animal water, air, or surface.

In yet other embodiments, the present methods may also be used on foods and plant species to reduce surface microbial populations; used at manufacturing or processing sites handling such foods and plant species; or used to treat process waters around such sites. For example, the present methods may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The present methods may be used to treat transport waters such as those found in flumes, pipe transports, cutters, slicers, blanchers, retort systems, washers, and the like. Particular foodstuffs that may be treated with the present methods include eggs, meats, seeds, leaves, fruits and vegetables. Particular plant surfaces include both harvested and growing leaves, roots, seeds, skins or shells, stems, stalks, tubers, corms, fruit, and the like. The present methods may also be used to treat animal carcasses to reduce both pathogenic and non-pathogenic microbial levels.

In yet other embodiments, the present methods may be useful in the cleaning or sanitizing of containers, processing facilities, or equipment in the food service or food processing industries. The present methods may be used on food packaging materials and equipment, including for cold or hot aseptic packaging. Examples of process facilities in which the present methods may be employed include a milk line dairy, a continuous brewing system, food processing lines such as pumpable food systems and beverage lines, etc. Food service wares may be disinfected with the present methods. For example, the present methods may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

In yet other embodiments, the present methods may also be used on or in other industrial equipment and in other industrial process streams such as heaters, cooling towers, boilers, retort waters, rinse waters, aseptic packaging wash waters, and the like. The present methods may be used to treat microbes and odors in recreational waters such as in pools, spas, recreational flumes and water slides, fountains, and the like.

In yet other embodiments, a filter containing the peroxyhydroxycarboxylic acid compositions of the present invention may be used to reduce the population of microorganisms in air and liquids. Such a filter may be used to remove water and air-borne pathogens such as *Legionella*.

In yet other embodiments, the present methods may be employed for reducing the population of microbes, fruit flies, or other insect larva on a drain or other surface.

In yet other embodiments, the present methods may also be employed by dipping food processing equipment into the peroxyhydroxycarboxylic acid composition or solution of the present invention, soaking the equipment for a time sufficient to sanitize the equipment, and wiping or draining excess composition or solution off the equipment. The present methods may be further employed by spraying or wiping food processing surfaces with the peroxyhydroxycarboxylic acid composition or solution, keeping the surfaces wet for a time sufficient to sanitize the surfaces, and removing excess composition or solution by wiping, draining vertically, vacuuming, etc.

In yet other embodiments, the present methods may also be used for sanitizing hard surfaces such as institutional type equipment, utensils, dishes, health care equipment or tools, and other hard surfaces. The present methods may also be employed in sanitizing clothing items or fabrics which have become contaminated. The peroxyhydroxycarboxylic acid compositions can be contacted with any contaminated surfaces or items at use temperatures in the range of about 4° C. to 60° C., for a period of time effective to sanitize, disinfect, or sterilize the surface or item. For example, the peroxyhydroxycarboxylic acid compositions may be injected into the wash or rinse water of a laundry machine and contacted with contaminated fabric for a time sufficient to sanitize the fabric.

Excess composition may be removed by rinsing or centrifuging the fabric.

In yet other embodiments, the peroxyhydroxycarboxylic acid compositions of the present invention may be applied to microbes or to soiled or cleaned surfaces using a variety of methods. These methods may operate on an object, surface, in a body or stream of water or a gas, or the like, by contacting the object, surface, body, or stream with the diluted (or use) composition. Contacting may include any of numerous methods for applying a composition, such as spraying the composition, immersing the object in the composition, foam or gel treating the object with the composition, or a combination thereof.

In yet other embodiments, the peroxyhydroxycarboxylic acid compositions of the present invention may be employed for bleaching.

In yet other embodiments, other hard surface cleaning applications for the peroxyhydroxycarboxylic acid compositions of the present invention include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

The concentrations of peroxyhydroxycarboxylic acid and/or hydrogen peroxide in the peroxyhydroxycarboxylic acid compositions of the present invention can be monitored in any suitable manner. In some embodiments, the concentrations of peroxyhydroxycarboxylic acid and/or hydrogen peroxide in the peroxyhydroxycarboxylic acid and/or hydrogen peroxide compositions can be monitored using a kinetic assay procedure, e.g., the exemplary procedure disclosed in U.S. Pat. Nos. 8,017,409 and 8,236,573. This can be accomplished by exploiting the difference in reaction rates between peroxyhydroxycarboxylic acid and hydrogen peroxide when using, for example, a buffered iodide reagent to differentiate peroxyhydroxycarboxylic acid and hydrogen peroxide concentrations when both these analyte compounds are present in the use composition. The monitor may also determine the concentrations of peroxyhydroxycarboxylic acid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

Methods for Treating a Biofilm

In yet another aspect, the present invention is directed to a method for treating a biofilm, which method comprises contacting a biofilm on a surface with an effective amount of peroxyhydroxycarboxylic acid for a sufficient time to stabilize, reduce and/or remove microbial population in and/or on said treated biofilm, or to stabilize, reduce and/or remove said biofilm on said surface.

The present methods can be used to treat a biofilm in any suitable location or environment. In some embodiments, the present methods can be used to treat a biofilm located on or inside a human environment, such as a biofilm located on or inside a shower room or site, a water pipe, a sewage pipe, a floor, a counter, or a part of human body. For example, the present methods can be used to treat a biofilm located on or inside a dental plaque, a part of a urinary tract, a part of a middle ear, or a part of gums. In other embodiments, the present methods can be used to treat a biofilm located on or inside a cooling- or heating-water system. In still other embodiments, the present methods can be used to treat a biofilm located on or inside an engineering system, e.g., a pipeline of oil and gas industry. In still other embodiments, the present methods can be used to treat a biofilm located on or inside a vehicle, e.g., an automobile, a boat or a ship. In yet other embodiments, the present methods can be used to treat a biofilm located on or inside a plant. In yet other embodiments, the present methods can be used to treat a biofilm located on or inside a consumer product, e.g., a contact lens or a pair glasses. In yet other embodiments, the present methods can be used to treat a biofilm located on or inside a medical device, e.g., an implantable medical device. Exemplary implantable medical devices include a catheter, a prosthetic cardiac valve or an intrauterine device. In yet other embodiments, the present methods can be used to treat a biofilm located on or inside a membrane, e.g., an ultrafiltration membrane (UF) membrane.

The present methods can use any suitable concentration of peroxyhydroxycarboxylic acid. In some embodiments, the present methods can comprise contacting a biofilm on a surface with from about 10 ppm to about 1,000 ppm peroxyhydroxycarboxylic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyhydroxycarboxylic acid.

The present methods can comprise contacting a biofilm on a surface with an effective amount of peroxyhydroxycarboxylic acid for any suitable amount of time. In some embodiments, the present methods can comprise contacting a biofilm on a surface with an effective amount of peroxyhydroxycarboxylic acid for from about 1 minute to about 10 hours, e.g., about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In an aspect, the contacting occurs for a period of time before degradation of the peroxyhydroxycarboxylic acid composition.

The present methods can be used to treat a biofilm made of or from any suitable microbial population. In some embodiments, the present method can be used to treat a biofilm made of or from a prokaryotic microbial population, e.g., a bacterial or an archaeal population. Exemplary bacterial populations include a population of *Pseudomonas aeruginosa, Streptococcus mutans, Streptococcus pneumoniae*, a *Legionella* bacteria, or a *Bacillus* bacteria, e.g., *Bacillus* sp. Spore. In other embodiments, the present method can be used to treat a biofilm made of or from a eukaryotic microbial population, e.g., a protozoal or fungal population. In still other embodiments, the present method can be used to treat a biofilm made of or from a viral population.

Methods for High Level Disinfecting, e.g. Endoscope and Other Instrument Reprocessing In yet another aspect, the various methods for treatment using the peroxyhydroxycarboxylic acid generated according to the methods of the invention can be employed for high level disinfectant applications, including sterilizing medical devices. The rate of formation of the peroxyhydroxycarboxylic acid in situ is particularly beneficial for the application of use for high level disinfection. The disinfectant is generated in situ and provides on demand disinfectant. Beneficially, the methods employing the high level disinfectant do not require high pressure and temperature required to achieve sterility. In an embodiment, the surface, such as an instrument, in need of treatment is contacted with an effective amount of peroxyhydroxycarboxylic acid for a sufficient time to stabilize, reduce and/or remove microbial population in and/or on said treated surface, or to stabilize, reduce and/or remove soils and microbes on said surface.

In an aspect, the methods allow for repurposing or reuse of the surface through disinfection and/or sanitizing of the surface, such as an instrument. Exemplary surfaces, including instruments suitable for reprocessing according to the invention include any instrument, including medical or dental instruments or devices that can benefit from cleaning with a composition according to the present invention. Particularly suitable instruments include, but are not limited to: diagnostic instruments, scopes (e.g., endoscopes, stethoscopes, and arthroscopes) and related equipment, and the like, or combinations thereof.

The present methods can use any suitable concentration of peroxyhydroxycarboxylic acid. In some embodiments, the present methods can comprise contacting a surface with from about 10 ppm to about 1,000 ppm peroxyhydroxycarboxylic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyhydroxycarboxylic acid. In a preferred aspect, the methods of contacting provide from about 10 ppm to about 500 ppm peroxyhydroxycarboxylic acid for high level disinfectant generated in situ within a matter of minutes.

The present methods can comprise contacting a surface with an effective amount of peroxyhydroxycarboxylic acid for any suitable amount of time. In some embodiments, the present methods can comprise contacting a surface with an effective amount of peroxyhydroxycarboxylic acid for from about 1 minute to about an hour, e.g., about 1 minute, 2 minutes, 3 minutes, 4 minutes, 5 minutes, 6 minutes, 7 minutes, 8 minutes, 9 minutes, or 10 minutes or greater. In an aspect, the contacting time is preferably less than 10 minutes, and more preferably less than 5 minutes. In an aspect, the contacting occurs for a period of time before degradation of the peroxyhydroxycarboxylic acid composition.

The present methods can be used to treat a surface for instrument reprocessing having a contaminated surface from any suitable microbial populations. In some embodiments, the present method can be used to treat a surface made of or from a prokaryotic microbial population, e.g., a bacterial or an archaeal population. Exemplary bacterial populations include a population of *Pseudomonas aeruginosa, Streptococcus mutans, Streptococcus pneumoniae*, a *Legionella* bacteria, or a *Bacillus* bacteria, e.g., *Bacillus* sp. Spore. In other embodiments, the present method can be used to treat a surface made of or from a eukaryotic microbial population, e.g., a protozoal or fungal population. In still other embodiments, the present method can be used to treat a surface made of or from a viral population.

The present methods can be conducted at any suitable temperature range. In some embodiments, the present methods can be conducted at a temperature ranging from about 20° C. to about 40° C., e.g., about 20° C.-25° C., 25° C.-30° C., 30° C.-35° C., or 35° C.-40° C., or ambient conditions. The present methods are preferably conducted at a near neutral pH of the peroxyhydroxycarboxylic acid compositions to avoid corrosion of the treated surfaces. In some embodiments, the pH is from about 4-9, 4.5-5.5, and preferably 5.5-6.5. In a preferred aspect, the methods are conducted at near neutral pH and thereby reduces and/or eliminates risk of corrosion to the surfaces being treated.

Beneficially, the methods of high level disinfection are suitable for in situ generation of the peroxyhydroxycarboxylic acid under conditions suitable for the disinfection. In an aspect, the peroxyhydroxycarboxylic acid is generated and used within a matter of minutes at a point of use.

Methods for Treating a Target or Surface Using a Saturated Wipe

In yet another aspect, the various methods for treatment using the peroxyhydroxycarboxylic acid generated according to the methods of the invention can be delivered using a saturated wipe. Disposable substrates are commonly used in cleaning applications. Suitable substrates include woven and nonwoven fabrics and various combinations thereof. Such substrates can be impregnated with the peroxyhydroxycarboxylic acid generated compositions according to the invention or with the generated peroxyhydroxycarboxylic acid at a point of use for application using the substrate. The resulting disinfecting products fabricated from such impregnated substrates are accepted as a convenient and practical means for cleaning surfaces, such as disclosed in U.S. Patent Publication No. 2014/0271762 which is incorporated herein by reference in its entirety.

In an embodiment, microfiber products are used herein for the delivery of the peroxyhydroxycarboxylic acid for consumer cleaning, such as those constructed from split conjugated fibers of polyester and polyamide, or alternatively polyamide free versions. In an aspect, the peroxyhydroxycarboxylic acid generated according to the methods of the invention is used to coat the substrate for contacting a surface. In another aspect, a portion of the reagents for the peroxyhydroxycarboxylic acid generating composition is/are impregnated into the substrate which thereafter contacts the remaining reagents to generate the peroxyhydroxycarboxylic acid composition at a point of use by a user.

The peroxyhydroxycarboxylic acid (or reagents) coated onto the substrate may optionally further include one or more additives such as fragrances, dyes, pigments, emollients, bleaching agents, anti-static agents, anti-wrinkling agents, odor removal/odor capturing agents, ultraviolet light protection agents, insect repellency agents, souring agents, mildew removing agents, allergicide agents, and mixtures thereof.

In an embodiment, disinfectants are coated onto the substrate for length of times from about 20 seconds, 30 seconds, 45 seconds, 1 minute, 2 minutes, 5 minutes, 10 minutes and up to about 7 days. Pre-coated wipes may be sold in airtight containers. Such pre-coated wipes may be in contact with the disinfectant for seconds, to hours to days, and preferably up to one week with the peroxyhydroxycarboxylic acid according to the invention.

Methods for Skin and Surface Sanitizing and Disinfecting

In yet another aspect, the various methods for treatment using the peroxyhydroxycarboxylic acid generated according to the methods of the invention can be employed for skin sanitizing and disinfectant, including for example methods for mastitis control. The rate of formation of the peroxyhydroxycarboxylic acid in situ is particularly beneficial for the application of use for skin disinfection. In an embodiment, the surface, including skin or other external or mucosal surfaces of an animal in need of disinfectant is contacted with an effective amount of peroxyhydroxycarboxylic acid for a sufficient time to reduce and/or remove microbial population on said treated surface.

The present methods can use any suitable concentration of peroxyhydroxycarboxylic acid for disinfecting skin by applying a liquid, namely a solution, to the skin surface. In some embodiments, the present methods can comprise contacting a surface with from about 10 ppm to about 1,000 ppm peroxyhydroxycarboxylic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm peroxyhydroxycarboxylic acid. In a preferred aspect, the methods of contacting provide from about 10 ppm to about 500 ppm peroxyhydroxycarboxylic acid for disinfectant generated in situ within a matter of minutes.

The present methods can comprise contacting a surface with an effective amount of peroxyhydroxycarboxylic acid for any suitable amount of time. In some embodiments, the present methods can comprise contacting a surface with an effective amount of peroxyhydroxycarboxylic acid for from about 1 minute to about an hour, e.g., about 1 minute, 2 minutes, 3 minutes, 4 minutes, 5 minutes, 6 minutes, 7 minutes, 8 minutes, 9 minutes, or 10 minutes or greater. In an aspect, the contacting time is preferably less than 10 minutes, and more preferably less than 5 minutes. In an aspect, the contacting occurs for a period of time before degradation of the peroxyhydroxycarboxylic acid composition.

The present methods can be used to treat a surface, including skin, having a contaminated surface from any suitable microbial populations. In some embodiments, the present method can be used to treat a surface made of or from a prokaryotic microbial population, e.g., a bacterial or an archaeal population. Exemplary bacterial populations include a population of *Staphylococcus aureus, Streptococcus agalactiae, Streptococcus dysagalactiae,* and *Streptococcus uberis*. The methods are suitable for disinfecting common mastitis causing pathogens, including both contagious and environmental pathogens. Contagious bacteria, such as *Streptococcus agalactiae* and *Staphylococcus aureus*, primarily colonize host tissue sites such as mammary glands, teat canals, teat skin lesions etc. and are spread from one infected cow to another during the milking process. Environmental bacteria, often streptococci, enterococci and coliform organisms, are commonly present within the cow's surroundings from sources such as cow feces, soil, plant material, bedding or water, and infect by casual opportunistic contact with an animal during the inter-milking period.

The methods of disinfecting a skin surface may include the contacting of a surface with an effective amount of the disinfecting composition by various routes of application. In an aspect, the disinfectant composition can contact the surface by dipping the skin surface (such as teats) in solution, spray applying the solution to the surface, or by dipping in a foam produced from the solution. In a preferred aspect, a method of treating teats of lactating animals comprises applying an effective amount of the composition by dipping the teats in solution, spray applying the solution to teats, or by dipping in a foam produced from the solution.

In a preferred aspect, polyols include glycerin, propylene glycol, sorbitol, polyglycerol, and mixtures thereof can be combined with the peroxyhydroxycarboxylic acid compositions. In a preferred aspect, the surface is contacted with a disinfectant liquid, including a solution comprising the peroxyhydroxycarboxylic acid and the polyol in an amount from about 0.5 wt-% to about 50 wt-% of the disinfectant liquid. In a preferred aspect, the surface is contacted with a disinfectant liquid, including a solution comprising the peroxyhydroxycarboxylic acid and the polyol in an amount from about 1 wt-% to about 10 wt-% of the disinfectant liquid.

In some embodiments, the present methods can further comprise contacting the surface with the peroxyhydroxycarboxylic acid composition further comprising surface wetting agents. The surfactant or surfactant admixture of the present invention can be selected from compatible water soluble or water dispersible nonionic, or anionic surface-active agents; or mixtures of each or both types. Nonionic and anionic surfactants offer diverse and comprehensive commercial selection, low price; and most important, excellent detersive effect—meaning surface wetting. Surface—active or "wetting agents" function to increase the penetrant activity of the invention into the tissue surface at risk from mastitis causing pathogens. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Also useful are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counterions) associated with these polar groups, sodium, lithium and potassium impart water solubility and are most preferred in compositions of the present invention. Examples of suitable synthetic, water soluble anionic compounds are the alkali metal (such as sodium, lithium and potassium) salts or the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl naphthalene sulfonate, dialkyl naphthalene sulfonate and alkoxylated derivatives. Other anionic detergents are the olefin sulfonates, including long chain alkene sulfonates, long chain hydroxyalkane sulfonates or mixtures of alkenesulfonates and hydroxyalkanaesulfonates and alkylpoly (ethyleneoxy) ether sulfonates. Also included are the alkyl sulfates, alkyl poly (ethyleneoxy) ether sulfates and aromatic poly (ethyleneoxy) sulfates such as the sulfates or condensation products of ethylene oxide and nonyl phenol (usually having 1 to 6 oxyethylene groups per molecule).

In an aspect, oxidatively susceptible or acid hydrolytically susceptible surfactants are employed as wetting agents. Exemplary oxidatively susceptible surfactants comprise polyethylene glycol based surfactant, polyglycerol, polyol sugar based surfactants, and mixtures thereof. Exemplary surfactants include, alcohol ethoxylates, EO/PO copolymers exemplified by poloxamers, glycerol and polyglycerol ester surfactants, polysorbate surfactants exemplified by Tween® surfactants, and sugar based surfactants exemplified by alkyl polyglucosides such as Glucopon® surfactants. Additional disclosure of suitable wetting agents is set forth in U.S. Pat. No. 6,749,869 and Reissue No. RE41279E, each of which are herein incorporated by reference in their entirety. Beneficially, the disinfectant compositions are stable with peroxyhydroxycarboxylic acid compositions generated in situ, unlike conventional food based or skin friendly surfactants which are not stable in highly oxidative or very low pH environments of traditional equilibrium or concentrate peracids.

In some embodiments, the present methods can further comprise contacting the surface with the peroxyhydroxycarboxylic acid composition further comprising a dye or colorant. In an aspect, the peroxyhydroxycarboxylic acid of the disinfectant composition is provided with a dye or colorant to provide a mechanism for color marking of the disinfectant composition. Beneficially, the peroxyhydroxycarboxylic acid generated in situ does not have shelf-stability and formulation incompatibility with traditional colorants, as is experienced with traditional equilibrium and concentrate peracid systems. In an aspect, the dye or colorant is a food and/or drug additive dye. In an aspect, the dye or colorant is not a color changing or indicator system. In an aspect, complexed iodines offer the advantage of being chromophoric, i.e. easily visible when applied onto the skin. Other antimicrobial agents do not have this feature; therefore, compositions may include a water soluble or dispersible coloring agent (dye or pigment or mixtures) which renders the composition chromophoric, having sharp contrast to teat skin and permitting the dairy herd manager to visually discern that the teats have been treated.

In further aspects, the disinfectant compositions may be comprised of any number of optional ingredients. Generally, in accordance with the invention, there may be included within this composition formulary adjuvants which assist in the application of the invention with respect to physical and chemical stability, barrier film formation, skin or teat health maintenance, performance, physical form and manufacturing process anesthetics. Of course, these functions may be accomplished exclusively by composition ingredients already described or admixtures thereof; however, formulary or application or performance situations may occur requiring additional effect which may be accomplished by introducing an additional inorganic or organic agent or agents and mixtures thereof into the composition.

The compositions may optionally include medicaments, for example sunscreens such as paraamino benzoic acid and healing agents such as allantoin or urea to provide curative action and stimulation of formation of new tissue; preservatives such as methyl paraben, propyl paraben, sorbic and benzoic acids or salts thereof to retard bacterial growth and prolong shelf life; antioxidants such as BHT (butylated hydroxytoluene), BHA (butylated hydroxyanisole), TBHQ (tert-butylhydroquinone), or propyl gallate to retard oxidative or hydrolytic degradation; sequestering agents such as aminopolyacetates, polyphosphonates, aminpolyphosphonates, polycarboxylates, and condensed phosphates; dispersants or suspending agents having polyelectrolytic character such as polyacrylate and similar polycarboxylates of homopolymeric or copolymeric structure; and manufacturing processing agents, for example defoam additives employed to facilitate blending and mixing.

A wide variety of ingredients useful in skin disinfection, including mastitis control, treatment can be included in the compositions hereof. This list is not intended to be exhaustive and other optional ingredients, which may not be listed, but which are well known in the art, may also be utilized in the composition. The examples are not intended to be limited in any way. In certain cases, some of the individual adjuvants may overlap other categories. The adjuvants employed will be selected so as not to interfere with the antimicrobial action of the composition and to avoid physical or chemical instability of the product.

The present methods can be conducted at any suitable temperature ranges as disclosed herein. In general, the pH of bovine mastitis control treatments can vary from a low of about pH 2.0 to a maximum of approximately 11.0 depending primarily upon the choice of antimicrobial agent being incorporated in the composition because optimal efficacy normally occurs with a specific, narrow, pH range. Therefore the buffering agent or system is chosen accordingly. In some embodiments, the pH is from about 2-9, 3-8, and preferably 4-7.

Methods for Treating and/or Bleaching Laundry Articles

In an aspect, the peroxyhydroxycarboxylic acid compositions are suitable for treating laundry soils and cleaning articles, e.g., textiles, which have become soiled. In an aspect, additional functional ingredients, including those set forth in U.S. Publication No. 2013/0247308 (which is herein incorporated by reference in its entirety) can optionally be used in combination with the peroxyhydroxycarboxylic acid compositions disclosed herein for laundry applications. The compositions of the present invention either in combination with additional functional ingredients, alone and/or in combination with additional cleaning agents, can be used to remove stains from any conventional textile, including but not limited to, cotton, poly-cotton blends, wool, and polyesters. The compositions can be used on any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

The laundry item can be processed in a laundry washing machine like a washer extractor or a tunnel washer. A washer extractor that can be used includes a drum having an interior for holding laundry, a motor constructed and arranged for rotating the drum, a water inlet for introducing water into the drum interior, a chemical inlet for introducing chemicals into the drum interior, a drain for allowing fluid to drain from the drum interior, and a processing unit constructed for operating the washer extractor. The processing unit can be constructed to provide a washing cycle for washing laundry with a cleaning and disinfecting composition solution of the first component, a rinsing cycle for removing at least a portion of the detergent use solution, and a treatment cycle for treating laundry with a bleaching composition of the second component.

In conventional, industrial and/or commercial laundry washing applications of use, the peroxyhydroxycarboxylic acid compositions can be employed for removing soils from a textile either inside or outside a washing machine, when employing a method of removing soils in a laundry application. In some aspects, when the composition is employed outside the washing machine it is used in a concentrated formulation. In other aspects, when the composition is employed inside the washing machine it is used in a diluted (or a highly diluted) formulation, such as within the wash liquor of a washing machine in order to remove soils from textiles.

In a conventional, industrial laundry washing facility, textile materials can be subjected to several treatment steps in an industrial sized laundry washing machine to provide cleaning. Exemplary treatment steps include a presoak or a prewash step, a wash step (e.g. soap and suds step), a rinse step for the removal of soil containing wash liquor, a bleach step (separate or in combination with the wash step), several optional rinse steps to remove the bleaching composition, an optional sour step to adjust the pH, softening step, and an extract step that often involves spinning the textiles to remove water. The compositions of the invention can be employed in such exemplary conventional prewash or pre-soak steps, washing steps, and/or alternatively be used in washing treatment steps that vary from such conventional processes. In addition, the compositions of the invention may be employed with a variety of laundry washing machines, including industrial, commercial and/or consumer machines (e.g. residential and/or home laundry washing machine).

The method for treating laundry according to the invention can be provided as part of an overall method for cleaning laundry according to the invention. That is, as part of a laundry cleaning operation, the compositions of the present invention can be used alone to treat the articles, e.g., textiles, or can be used in conjunction with conventional detergents suitable for the articles to be treated. A laundry cleaning process according to the invention can include the removal of soil, the removal of staining or the appearance of staining, and/or the reduction of a population of microbes. The compositions of the invention can be used with conventional detergents in a variety of ways. Such formulation can include, for example, detergents for a pre-wash or pre-soak step and/or a soap/suds/bleach step. In other embodiments, the compositions of the invention can be used to treat the article as a separate additive from a conventional detergent. The compositions can be provided in the form of a concentrate that is diluted with water to provide a use solution. Alternatively, the compositions can be provided in the form of a use solution (already diluted with water). When used as a separate additive, the compositions of the present invention can contact the article to be treated at any time. For example, the compounds and compositions of the invention can contact the article before, after, or substantially simultaneously as the articles are contacted with the selected detergent.

The use solution can be used for washing the articles. In an aspect, the compositions can be applied to a prewash step (e.g. a warm about 40-50° C.). In certain aspects, low water levels are employed for the warm prewash step. Thereafter the removal of the excess grease and oily soils from the surface of the article, the article can then be washed thoroughly in a main or conventional sud step (i.e. wash step) using detergents, bleaching agents and/or alkaline builders. In such embodiments, the compositions contact the article before the articles are contacted with the selected detergent, e.g. a pre-soak or a pre-wash situation, wherein the articles are contacted with the composition of the invention initially to emulsify soils on the substrate fabric. This step may include a contact time from at least a few minutes. This step may optionally include the use of a builder or component compositions for providing a source of alkalinity, such as to increase the pH from neutral to an alkaline pH, including for example a pH of at least 10, or at least 11 or greater. The step may be conducted at a broad range of temperatures.

In an embodiment, the compositions provides a suitable bleaching step, and may be combined with an additional bleaching and/or antimicrobial step. This bleaching and antimicrobial step can follow or precede steps of washing the laundry with a composition of the invention and draining and/or rinsing the composition solution from the laundry. In other applications, it is expected that the bleaching and antimicrobial step can occur simultaneously with the washing step. It is expected that in situations where the soiling is relatively light, it may be advantageous to combine the washing step employing the emulsifying composition of the invention with the bleaching and antimicrobial step. That is, the bleaching and antimicrobial step can include a soil removal step and/or it can occur before or after a soil removal step.

In an aspect of the invention, the composition is particularly suited for use as an additive composition within a regular wash/laundry process. For example, as disclosed herein the compositions can be employed as a bleaching agent or booster to a regular suds bath (regular wash/laundry process) which already contains a main detergent, alkalinity, and/or possibly bleach. Such exemplary processes are disclosed herein the description of the invention. Additional description of suitable laundry methods which may employ the compositions of the present invention are set forth, for example, in U.S. patent application Ser. No. 12/726,073, which is herein incorporated by reference in their entirety.

In an aspect, the peroxyhydroxycarboxylic acid composition is employed at a pH value of a use solution, such as in the drum of a washer extractor or in a tunnel washer, at a pH from about 7 to about 14, from about 7 to about 13, from about 7 to about 12, from about 7 to about 11, from about 7 to about 10, from about 7 to about 9, or from about 7 to about 8.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Perhydrolysis of Lactide.

Figure 2:
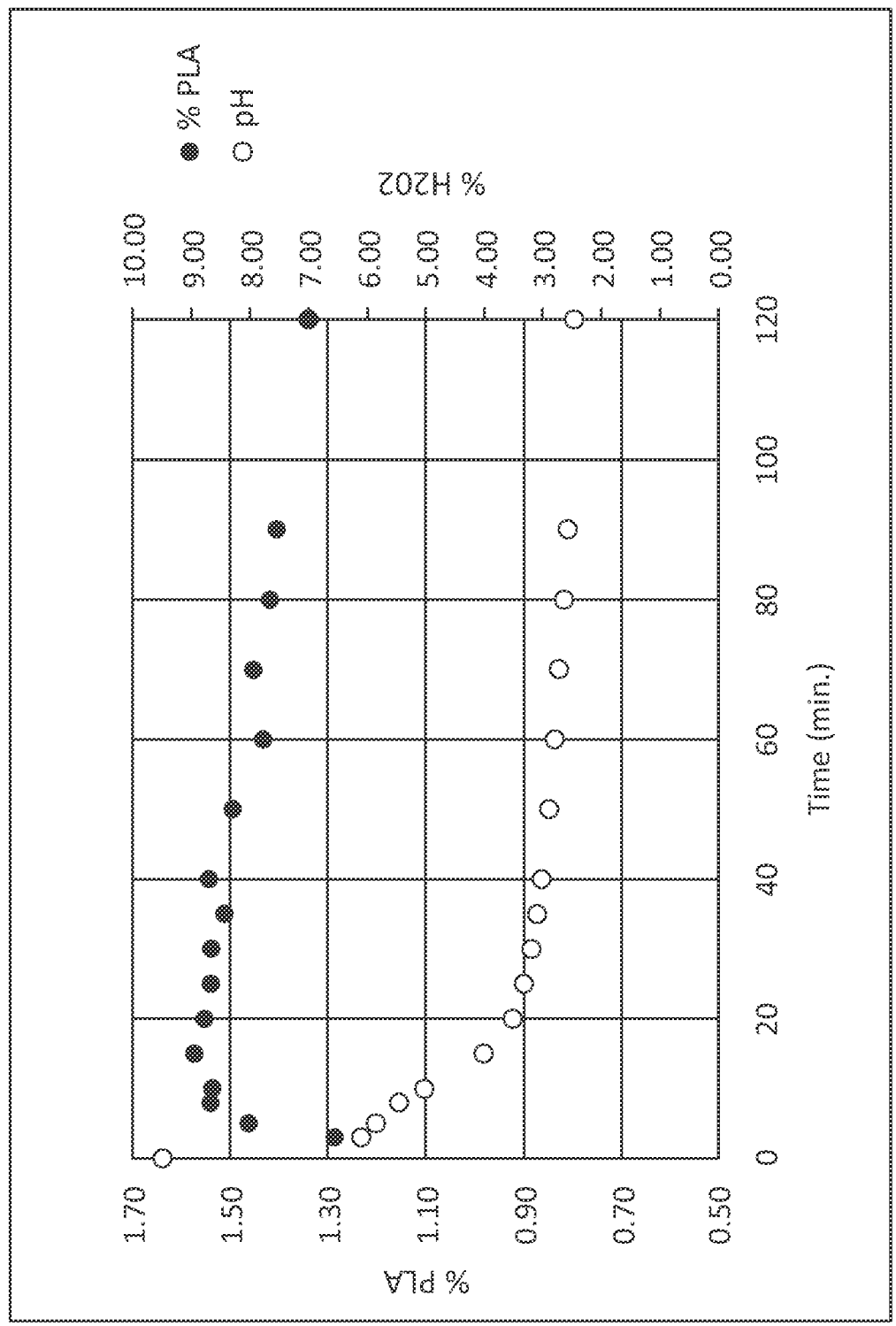
FIG. 2 illustrates the concentration of peroxylactic acid formed over time and the corresponding pH of the composition according to embodiments described herein.

2.5 grams of lactide was added to 50 grams of 2% $H_2O_2$ at pH 9.5 (adjusted with $Na_2CO_3$), and the mixture was stirred. The pH of the mixture was monitored, and the level of peroxylactic acid generated was titrated by iodometric titration. The results are summarized in Table 2 and shown in FIG. 2, where the reaction scheme is shown in FIG. 1.

TABLE 2

Generation Kinetic of Peroxylactic Acid through Perhydrolysis of Lactide

| Time (min) | Sample wt. (g) | Volume (ml) (0.1N $Na_2S_2O_3$) | % PLA | pH |
|---|---|---|---|---|
| 0 | NA | NA | 0.00 | 9.50 |
| 3 | 1.29 | 3.30 | 1.29 | 6.10 |
| 5 | 1.1 | 3.20 | 1.46 | 5.85 |
| 8 | 1.11 | 3.40 | 1.54 | 5.45 |
| 10 | 1.26 | 3.85 | 1.54 | 5.03 |
| 15 | 1.07 | 3.35 | 1.57 | 4.01 |
| 20 | 1.15 | 3.55 | 1.55 | 3.52 |
| 25 | 1.28 | 3.92 | 1.54 | 3.32 |
| 30 | 1.02 | 3.12 | 1.54 | 3.19 |
| 35 | 1.23 | 3.70 | 1.51 | 3.10 |
| 40 | 1.14 | 3.50 | 1.54 | 3.02 |
| 50 | 1.16 | 3.45 | 1.50 | 2.89 |
| 60 | 1.15 | 3.28 | 1.43 | 2.80 |
| 70 | 1.17 | 3.38 | 1.45 | 2.72 |
| 80 | 1.17 | 3.30 | 1.42 | 2.64 |
| 90 | 1.11 | 3.10 | 1.40 | 2.58 |
| 120 | 1.23 | 3.28 | 1.34 | 2.48 |
| 240 | 1.23 | 2.80 | 1.15 | 2.23 |
| 300 | 1.11 | 2.30 | 1.04 | 2.13 |
| 360 | 1.17 | 2.25 | 0.97 | 2.08 |

Beneficially as shown in Table 2 the lactide ester reacts with the hydrogen peroxide under mild alkaline conditions to provide rapid generation of peroxylactic acid. The initial measurement point for the peroxylactic acid generation was 3 minutes, however, the reaction is near instantaneous and generates the peroxylactic acid upon contact of the reagents under the conditions described. The depicted % PLA shows the reaction to provide a concentrate solution of the chemistry, which can thereafter be diluted for desired applications of use. As shown the rapid generation of the PLA and lactic acid and in high quantities results in decrease in pH of the concentrated solution.

Example 2

Perhydrolysis of Glycolide.

Figure 3:
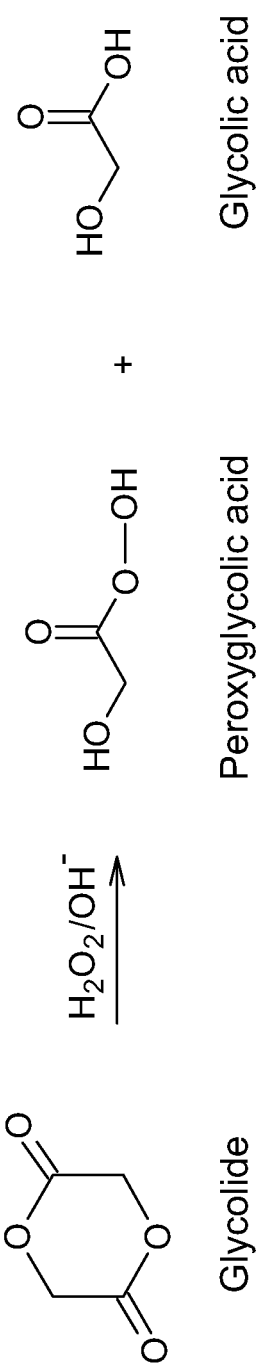
FIG. 3 illustrates perhydrolysis of glycolide to form peroxyglycolic acid according to embodiments described herein.

2.5 grams of glycolide was added to 50 grams of 2% $H_2O_2$ at pH 9.5 (sodium hydroxide provided as alkalinity and adjusted with $Na_2CO_3$), and the mixture was stirred. The pH of the mixture was monitored, and the level of peroxyglycolic acid generated was titrated by iodometric titration. The results are summarized in Table 3 and the reaction is scheme shown in FIG. 3.

TABLE 3

Generation Kinetic of Peroxyglycolic Acid through Perhydrolysis of Glycolide

| Time (min) | Sample wt. (g) | Volume (ml) (0.1N $Na_2S_2O_3$) | % PGA | pH |
|---|---|---|---|---|
| 0 | NA | NA | 0.00 | 9.50 |
| 1 | 1.17 | 6.85 | 2.69 | 5.30 |
| 3 | 0.67 | 4.00 | 2.75 | 3.42 |
| 5 | 0.79 | 4.62 | 2.69 | 3.00 |
| 10 | 0.76 | 4.35 | 2.63 | 2.65 |
| 20 | 0.72 | 4.10 | 2.86 | 2.37 |
| 25 | 1.28 | 3.92 | 1.54 | 3.32 |
| 30 | 1.02 | 3.12 | 1.54 | 3.19 |
| 35 | 1.23 | 3.70 | 1.51 | 3.10 |
| 40 | 1.14 | 3.50 | 1.54 | 3.02 |

Beneficially as shown in Table 3 the glycolide ester reacts with the hydrogen peroxide and caustic alkalinity (sodium hydroxide) to provide rapid generation of peroxyglycolic acid. In this example the initial measurement point for the peroxyglycolic acid generation was 1 minute, confirming that the reaction is near instantaneous and generates the peroxyglycolic acid upon contact of the reagents under the conditions described as described in Example 1.

Example 3

Comparison of Lactide Ester to Lactic Acid Precursor to Generate Peroxylactic Acid. The equilibrium reaction using lactic acid reagent for generating perlactic acid was performed to show the distinct advantages of the methods of generation according to the invention. The lactic acid reagent is inefficient and does not generate high concentrations of the peracid as the lactic acid and peroxide shows the hydroxyl groups reacting with peroxide. It is also known that the reaction results in additional byproducts—which may not be suitable for various applications of use. Table 4 shows the formulation used to generate the equilibrium composition of peroxylactic acid.

TABLE 4

Peroxylactic Acid Forming Composition through Equilibrium Reaction of Lactic Acid

| Component | wt. (g) | wt. % |
|---|---|---|
| Lactic acid (85%, ACS) | 25 | 81.7 |
| $H_2O_2$ (50%) | 5 | 16.3 |
| HEDP (60%) | 0.6 | 2.0 |
| DPA | 0.03 | 0.1 |
|  |  | 0.0 |
| Total | 30.6 | 100 |

Figure 4:
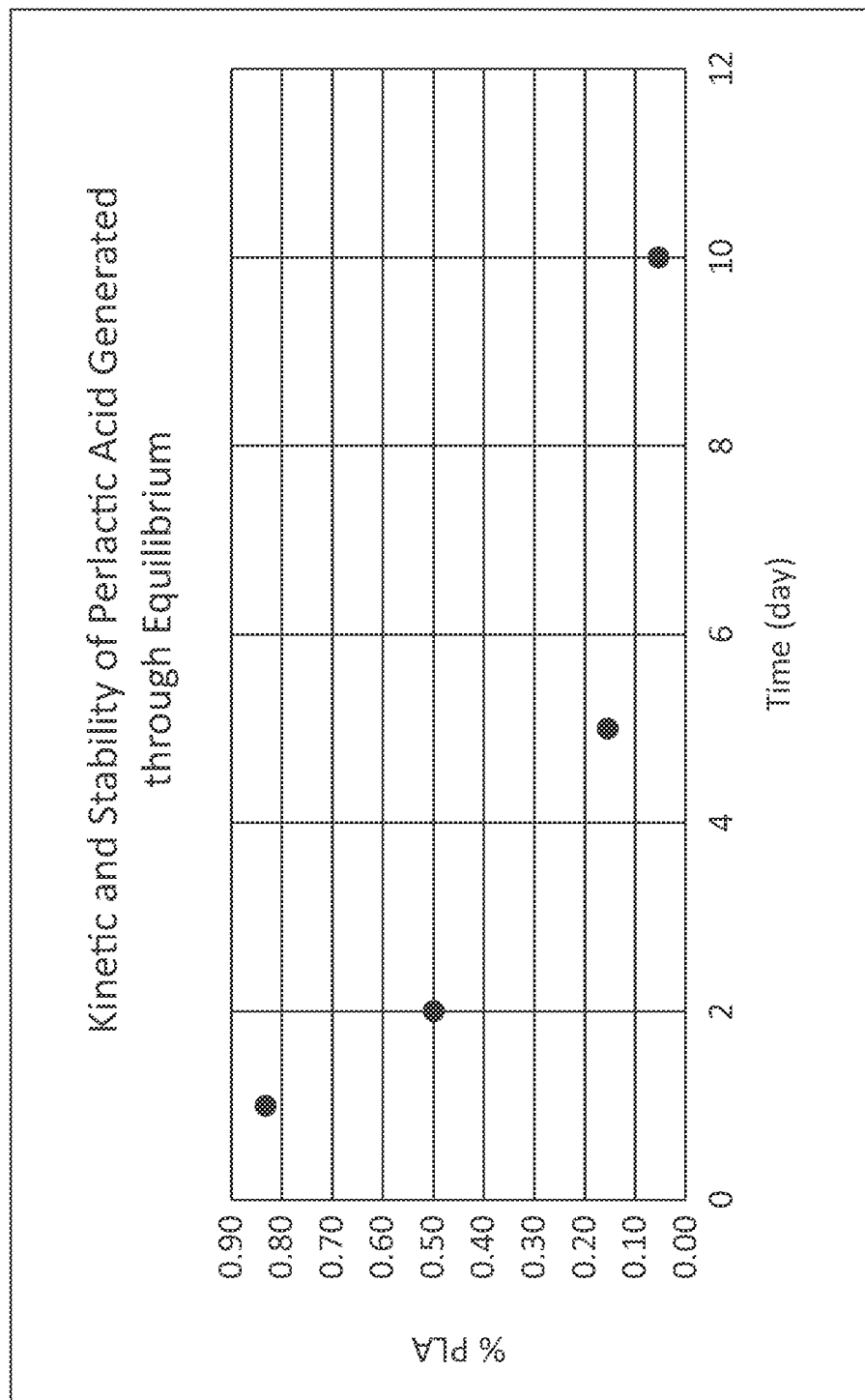
FIG. 4 shows the kinetic instability of peroxylactic acid generated through an equilibrium reaction of lactic acid and hydrogen peroxide.

As shown in FIG. 4, the yield of peroxylactic acid generated through the equilibrium between lactic acid and $H_2O_2$ is very low, furthermore, unlike the traditional peroxycarboxylic acid such as peroxyacetic acid, the generated perlactic acid is very unstable. This makes it commercially not feasible to deliver the compositions for end application at customer locations.

Example 4

Comparison of Lactide Ester to a Monoester Precursor (Ethyl Lactate) to Generate Peroxylactic Acid. The reaction using a monoester reagent for generating perlactic acid was performed to show the distinct advantages of the methods of generation according to the invention using a lactide ester. The monoester reagent—ethyl lactate—is inefficient and does not generate high concentrations of the peracid. It is also known that the reaction results in additional byproducts—which may not be suitable for various applications of use. Table 5 shows the formulation used to attempt to generate perlactic acid through the perhydrolysis of lactic acid ester, namely ethyl lactate under the alkaline conditions. The results are summarized in Table 6.

TABLE 5

Composition for Ethyl Lactate Perhydrolysis

| Composition | Wt-% |
|---|---|
| $H_2O_2$ | 1 |
| Water | 90.0 |
| pH adjusted to 11 with NaOH | |
| Ethyl lactate | 9 |
| Total | 100 |

TABLE 6

Iodometric Titration of Ethyl Lactate Perhydrolysis Reaction

| Time | Sample Wt. (g) | V mL (0.1N $Na_2S_2O_3$) | % PLA | pH |
|---|---|---|---|---|
| 5 min. | 1.06 | 0.00 | 0.00 | 9.41 |
| 10 min. | 1.63 | 0.00 | 0.00 | 8.45 |
| 60 min. | 1.87 | 0.00 | 0.00 | 5.23 |

As demonstrated in the Table 6, unlike lactide used to produce peroxylactic acid in Examples 1-2, the ethyl lactate does not perhydrolysis to generate perlactic acid, instead it only hydrolysis to generate lactic acid as evidenced by the changes of the pH.

Example 5

Antimicrobial Efficacy of Peroxylactic Acid.

The antimicrobial efficacy of generated peroxylactic acid was evaluated following the US EPA food contact suspension test protocol (AOAC 960.09) against *Staphylococcus aureus* and *Escherichia coli* according to the conditions set forth in Table 7.

TABLE 7

| Test Parameters | |
|---|---|
| Test System: | *Staphylococcus aureus* ATCC 6538 |
| | *Escherichia coli* ATCC 11229 |
| Test Substance Diluent: | 500 ppm Synthetic Hard Water, pH 7.71 |
| Test Substances: | A. 25 ppm PLA |
| | B. 50 ppm PLA |
| | C. 100 ppm PLA |
| | D. 150 ppm PLA |
| | E. 200 ppm PLA |
| Exposure Time (seconds): | 30 seconds |
| Neutralizer: | 9 mL DE Broth |
| Test Temperature: | Ambient (18-20° C.) |
| Plating Medium: | TSA |
| Incubation: | 35° C. for 48 hours |

The efficacy of the various concentrations of peroxylactic acid generated from lactide precursor as described in Example 1 are shown in Tables 8-9, demonstrating micro efficacy (log reduction) achieved from peroxylactic acid compositions at varying concentrations and varying plate dilutions.

TABLE 8

Micro Efficacy Results against *S. aureus*

| Test Substance | Exposure Time | Plate Count | Plate Dilution | CFU/ml | $Log_{10}$ Growth | Average $Log_{10}$ Growth | $Log_{10}$ Reduction |
|---|---|---|---|---|---|---|---|
| 50 ppm PLA | 30 seconds | TNTC | 10000 | >3.00E+06 | >6.48 | >6.48 | <1.32 |
| | | TNTC | 10000 | >3.00E+06 | >6.48 | | |
| 100 ppm PLA | | 124 | 1000 | 1.24E+05 | 5.09 | 5.22 | 2.58 |
| | | 22 | 10000 | 2.20E+05 | 5.34 | | |
| 150 ppm PLA | | 92 | 10 | 9.20E+02 | 2.96 | 2.82 | 4.98 |
| | | 48 | 10 | 4.80E+02 | 2.68 | | |
| 200 ppm PLA | | 0 | 10 | <1.00E+01 | <1.00 | <1.00 | >6.80 |
| | | 0 | 10 | <1.00E+01 | <1.00 | | |
| Inoculum Numbers | | 59 | 1000000 | 5.90E+07 | 7.77 | 7.80 | |
| | | 68 | 1000000 | 6.80E+07 | 7.83 | | |
| Neutralizer Control "A" - 200 ppm PLA | | 56 | 1 | 5.6E+01 | 1.75 | Pass | |
| Neutralizer Control "B" | | 48 | 1 | 4.80+01 | 1.68 | | |
| Neutralizer Control "C" | | 39 | 1 | 3.90+01 | 1.59 | | |

TABLE 9

Micro Efficacy Results against *E. coli*

| Test Substance | Exposure Time | Plate Count | Plate Dilution | CFU/ml | $Log_{10}$ Growth | Average $Log_{10}$ Growth | $Log_{10}$ Reduction |
|---|---|---|---|---|---|---|---|
| 25 ppm PLA | 30 seconds | 149 | 10 | 1.49E+03 | 3.17 | 3.25 | 4.64 |
| | | 21 | 100 | 2.10E+03 | 3.32 | | |
| 50 ppm PLA | | 0 | 10 | <1.00E+01 | <1.00 | <1.00 | >6.89 |
| | | 0 | 10 | <1.00E+01 | <1.00 | | |

TABLE 9-continued

Micro Efficacy Results against *E. coli*

| Test Substance | Exposure Time | Plate Count | Plate Dilution | CFU/ml | $Log_{10}$ Growth | Average $Log_{10}$ Growth | $Log_{10}$ Reduction |
|---|---|---|---|---|---|---|---|
| 100 ppm PLA | | 0 | 10 | <1.00E+01 | <1.00 | <1.00 | >6.89 |
| | | 0 | 10 | <1.00E+01 | <1.00 | | |
| Inoculum Numbers | | 77 | 1000000 | 7.70E+07 | 7.89 | 7.89 | |
| | | 79 | 1000000 | 7.90E+07 | 7.90 | | |
| Neutralizer Control "A" - 200 ppm PLA | | 66 | 1 | 6.60E+01 | 1.82 | Pass | |
| Neutralizer Control "B" | | 70 | 1 | 7.00E+01 | 1.85 | | |
| Neutralizer Control "C" | | 69 | 1 | 6.90E+01 | 1.84 | | |

TABLE 10

Antimicrobial Efficacy (FCS) Against *Listeria* and *Campylobacter*

| Test Substance | Exposure Time | Plate Count | Plate Dilution | CFU/ml | $Log_{10}$ Growth | Average $Log_{10}$ Growth | $Log_{10}$ Reduction |
|---|---|---|---|---|---|---|---|
| *Listeria monocytogenes* ATCC 49594 | | | | | | | |
| 50 ppm PLA | 30 second | 69 | 10000 | 6.90E+05 | 5.84 | 5.84 | 2.23 |
| | | 68 | 10000 | 6.80E+05 | 5.83 | | |
| 100 ppm PLA | | 0 | 10 | <1.00E+01 | <1.00 | <1.00 | >7.06 |
| | | 0 | 10 | <1.00E+01 | <1.00 | | |
| 150 ppm PLA | | 0 | 10 | <1.00E+01 | <1.00 | <1.00 | >7.06 |
| | | 0 | 10 | <1.00E+01 | <1.00 | | |
| Inoculum Numbers | | 114 | 1000000 | 1.14E+08 | 8.06 | 8.06 | |
| | | 116 | 1000000 | 1.16E+08 | 8.06 | | |
| *Campylobacter jejuni* ATCC 33291 | | | | | | | |
| 25 ppm PLA | 30 second | 7 | 10 | <1.00E+01 | <1.00 | <1.00 | >7.06 |
| | | 3 | 10 | <1.00E+01 | <1.00 | | |
| 50 ppm PLA | | 0 | 10 | <1.00E+01 | <1.00 | <1.00 | >7.06 |
| | | 0 | 10 | <1.00E+01 | <1.00 | | |
| 75 ppm PLA | | 0 | 10 | <1.00E+01 | <1.00 | <1.00 | >7.06 |
| | | 0 | 10 | <1.00E+01 | <1.00 | | |
| Inoculum Numbers | | 45 | 1000000 | 4.50E+07 | 7.65 | 7.66 | |
| | | 47 | 1000000 | 4.70E+07 | 7.67 | | |

Example 6

Antimicrobial Efficacy of Peroxylactic Acid.

The antimicrobial efficacy of peroxylactic acid was evaluated on chicken carcass against *Salmonella* in comparison to peroxyacetic acid (PAA). The test conditions are set forth in Table 11. The molecular weight of PLA is 106, and PAA 76, therefore the molar equivalent base of the peracids is 500 ppm PLA equals to 359 ppm PAA.

TABLE 11

| Test Parameters | |
|---|---|
| Test System: | *Salmonella* ser. Heidelberg, Newport and Braenderup (modified to be resistant to 50 μg/mL nalidixic acid) |
| Test Substance Diluent: | Cold tap water |
| Test Substances: | A. 500 ppm PAA (Insepxx 250, pH 4.15) |
| | B. 500 ppm PLA (pH 4.09) |
| | C. 1000 ppm PLA (pH 3.50) |
| | D. 2000 ppm PLA (pH 3.15) |

TABLE 11-continued

| Test Parameters | |
|---|---|
| Exposure Time (seconds): | 15 second dip |
| Neutralizer: | 50 mL DE Broth |
| Test Temperature: | Room Temperature |
| Plating Medium: | TSA + 50 μg/mL nalidixic acid |
| Incubation: | 35° C. for 24 hours |

The comparative efficacy of the peroxyacetic acid compared to various concentrations of peroxylactic acid generated from lactide precursor as described in Example 1 is shown in Table 12, demonstrating at least equivalent micro efficacy (log reduction) achieved from peroxylactic acid compositions at varying concentrations and varying plate dilutions, and improved micro efficacy at 1000 ppm peroxylactic acid. The data shows improved performance of the 1000 ppm over the 2000 ppm in the particular meat tissue. There can be test variation on different meat tissues, which is not uncommon.

TABLE 12

Micro Efficacy Results

| Test Substance | Drain Time | Rep | Plate Count | Plate Dilution | CFU/Surface (CFU/ml × 50) | $Log_{10}$ Survivors | Avg $Log_{10}$ Survivors | $Log_{10}$ Reduction | Standard Deviation |
|---|---|---|---|---|---|---|---|---|---|
| Tap Water | 30 minutes | 1 | 70 | 10000 | 3.50E+07 | 7.54 | 7.46 | 0.17 | 0.14 |
| | | 2 | 40 | 10000 | 2.00E+07 | 7.30 | | | |
| | | 3 | 67 | 10000 | 3.35E+07 | 7.53 | | | |
| 500 ppm PAA | | 1 | 87 | 1000 | 4.35E+06 | 6.64 | 6.54 | 1.09 | 0.14 |
| | | 2 | 47 | 1000 | 2.35E+06 | 6.37 | | | |
| | | 3 | 79 | 1000 | 3.95E+06 | 6.60 | | | |
| 500 ppm PLA | | 1 | 58 | 1000 | 2.90E+06 | 6.46 | 6.55 | 1.08 | 0.16 |
| | | 2 | 58 | 1000 | 2.90E+06 | 6.46 | | | |
| | | 3 | 109 | 1000 | 5.45E+06 | 6.74 | | | |
| 1000 ppm PLA | | 1 | 32 | 1000 | 1.60E+06 | 6.20 | 6.16 | 1.47 | 0.13 |
| | | 2 | 37 | 1000 | 1.85E+06 | 6.27 | | | |
| | | 3 | 21 | 1000 | 1.05E+06 | 6.02 | | | |
| 2000 ppm PLA | | 1 | 45 | 1000 | 2.25E+06 | 6.35 | 6.54 | 1.09 | 0.20 |
| | | 2 | 113 | 1000 | 5.65E+06 | 6.75 | | | |
| | | 3 | 67 | 1000 | 3.35E+06 | 6.53 | | | |
| Inoculated Meat Numbers | | 1 | 81 | 10000 | 4.05E+07 | 7.61 | 7.63 | | |
| | | 2 | 80 | 10000 | 4.00E+07 | 7.60 | | | |
| | | 3 | 96 | 10000 | 4.80E+07 | 7.68 | | | |
| Meat Background Numbers | | 1 | 1 | 1 | 5.00E+01 | <1.70 | <1.70 | | |
| | | 2 | 1 | 1 | 5.00E+01 | <1.70 | | | |
| Inoculum Numbers | | | 97 | 10000000 | | 8.99 | 9.00 | | |
| | | | 101 | 10000000 | | 9.00 | | | |

Example 7

Peroxylactic Acid Compositions.

Figure 5:
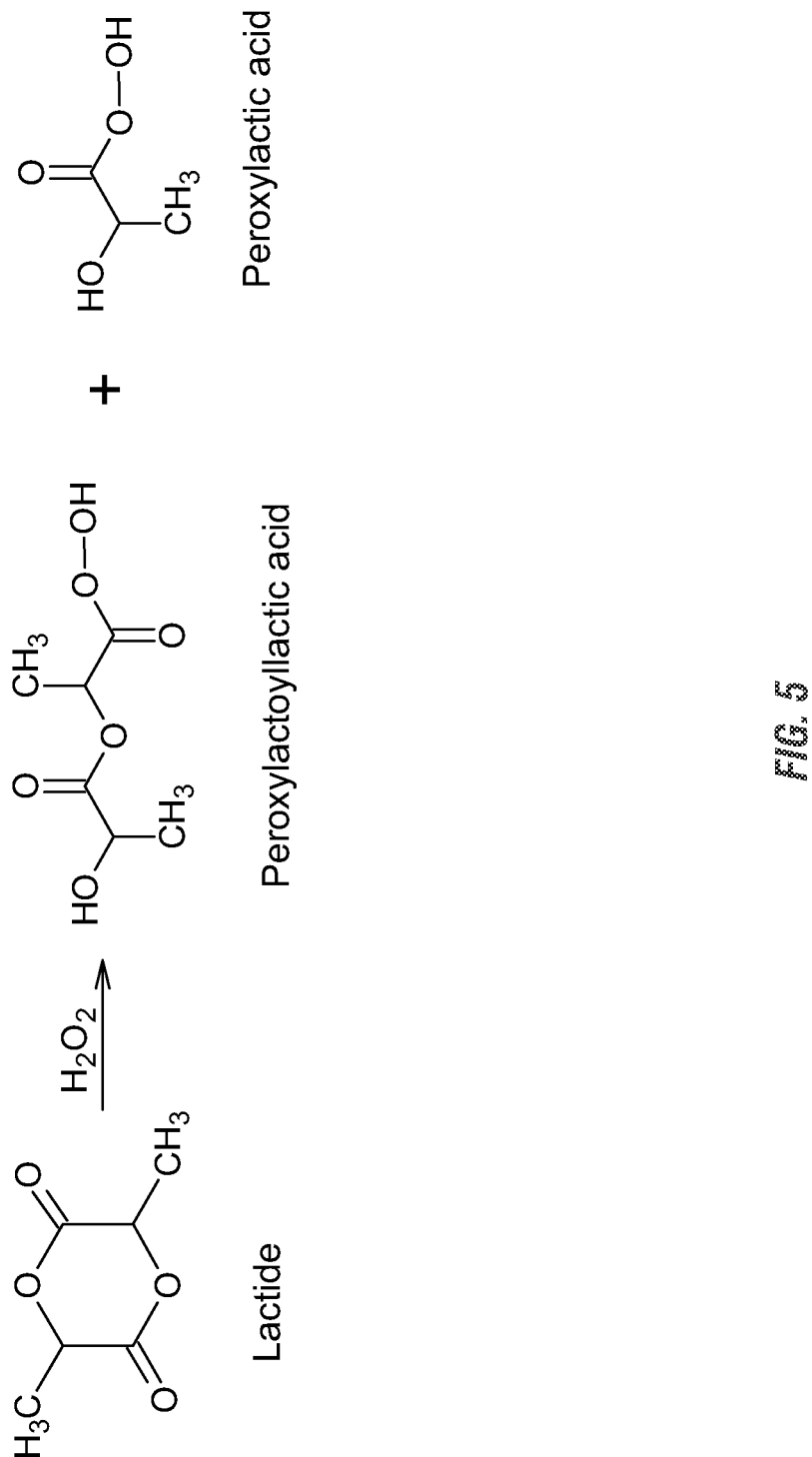
FIG. 5 shows additional structures in the peroxyalphahydroxycarboxylic acid compositions generated herein.

The lactide precursor for perhydrolysis as described herein generates a majority of peroxylactoyllactic acid in combination with the peroxylactic acid, as shown in FIG. 5. Initial HPLC estimation confirms up to about 85% peroxylactolylactic acid and about 15% peroxylactic acid (greater than 5:1 ratio; approximately 5.6:1 ratio), resulting in a novel peroxyalphahydroxycarboxylic acid composition.

This is different from the anticipated ratio of components, as commercial food grade lactic acid (88% active) contains 59% lactic acid and 29% lactoyllactic acid (2:1 ratio), characterized by both HPLC and NMR. In these the dimeric ester is treated and quantified as lactic acid, as on hydrolysis lactoyllactic acid (ester of the lactic acid) will slowly hydrolyze to free lactic acid (such as when diluted in an excess of water).

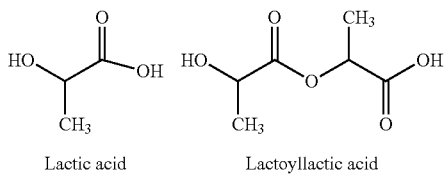

Lactic acid      Lactoyllactic acid

Example 8

Peroxylactic Acid Generation Kinetics from Solid Composition. The lactide precursor in a solid pellet with citric acid and sodium percarbonate were added to water for the perhydrolysis reaction to generate peroxylactic acid (PLA). The reaction kinetics were evaluated by dissolving approximately 2.5 gram pellet as shown in Table 13 in 500 mL DI water to measure PLA generation and pH over time.

TABLE 13

| Material | Wt. (grams) | Wt. % |
|---|---|---|
| Sodium percarbonate | 0.91 | 37.0 |
| Citric acid | 0.75 | 30.5 |
| Lactide | 0.80 | 32.5 |
| | 2.46 | 100 |

The PLA generation were measured on two occasions. Table 14 shows the first PLA generation kinetics and Table 15 shows the second PLA generation kinetics using the same batch of tablets stored under ambient conditions for 9 months. The initial testing point of 10 minutes provides time for the pellet to dissolve in the water so that PLA generation can begin.

TABLE 14

| Time (min.) | pH | Sample (g) | EP (mL) | PLA (ppm) |
|---|---|---|---|---|
| 10 | 6.06 | 22.43 | 0.5500 | 130 |
| 30 | 5.95 | 21.90 | 0.9160 | 222 |
| 60 | 5.64 | 25.13 | 1.1180 | 236 |
| 90 | 5.41 | 29.53 | 1.2080 | 217 |
| 120 | 5.23 | 21.62 | 0.8240 | 202 |
| 150 | 5.11 | 18.99 | 0.6740 | 188 |
| 180 | 5.01 | 19.26 | 0.6180 | 170 |
| 210 | 4.93 | 22.46 | 0.646 | 152 |
| 240 | 4.87 | 20.90 | 0.574 | 146 |

TABLE 15

| Time (min) | pH | Sample (g) | EP (mL) | PLA (ppm) |
|---|---|---|---|---|
| 10 | 5.74 | 4.59 | 0.1060 | 122 |
| 20 | 5.73 | 4.09 | 0.1160 | 150 |
| 30 | 5.69 | 4.11 | 0.1320 | 170 |
| 40 | 5.62 | 4.13 | 0.1540 | 198 |
| 50 | 5.58 | 4.13 | 0.1540 | 198 |
| 60 | 5.49 | 4.34 | 0.1640 | 200 |

TABLE 15-continued

| Time (min) | pH | Sample (g) | EP (mL) | PLA (ppm) |
|---|---|---|---|---|
| 120 | 5.25 | 4.09 | 0.1380 | 179 |
| 180 | Not measured | 4.84 | 0.146 | 160 |
| 240 | 4.82 | 4.20 | 0.102 | 129 |
| 300 | 4.74 | 4.57 | 0.088 | 102 |
| 360 | 4.68 | 4.98 | 0.08 | 85 |

Example 9

Figure 6:
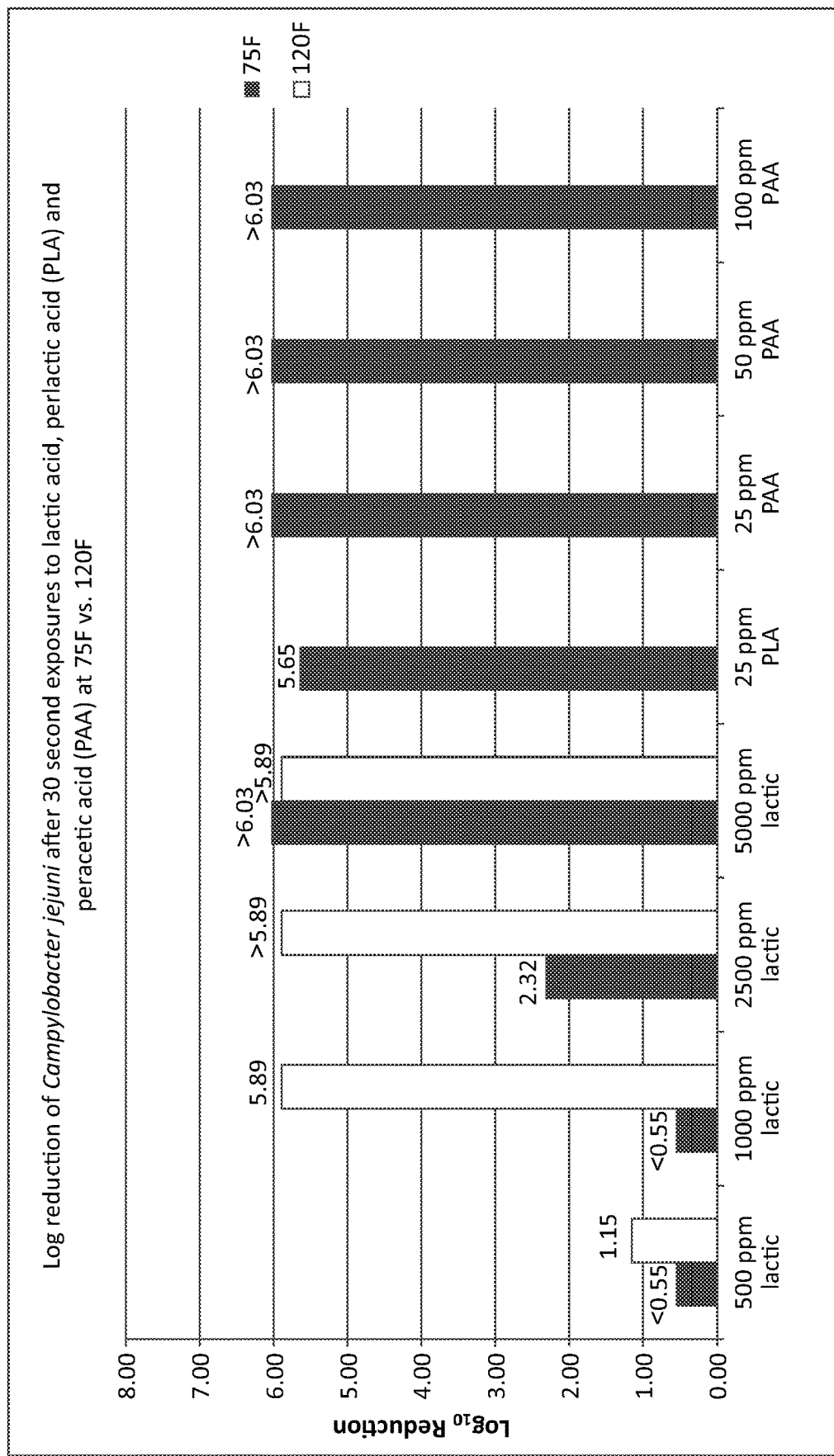
FIG. 6 shows efficacy of peroxylactic acid compared to lactic acid and peroxyacetic acid at various temperatures.

Additional efficacy testing against *Campylobacter jejuni* ATCC 33291 as described in Table 10 was completed to compare efficacy at 75° F. of lactic acid, peroxylactic acid (PLA) and peroxyacetic acid (PAA). The results are shown in FIG. 6, demonstrating that PLA at 25 ppm provides efficacy that substantially similar to PAA and significantly improved upon lactic acid. In particular, in comparison to lactic acid substantially lower concentrations are required (25 ppm PLA instead of approximately 5000 ppm lactic acid).

FIG. 6 also shows the lactic acid tested at the higher temperature of 120° F. This shows that again a significant concentration of lactic acid (1,000 ppm-5,000 ppm) are required for the at least 5 log reduction of the *C. jujuni*. As the PLA can be formed on site and then allowed to degrade into lactic acid, this demonstrates another pathway of use for the in situ generated chemistry. Beneficially, the concentration of peroxylactic acid required for micro efficacy are substantially lower than lactic acid and the lactic acid which is formed upon degradation of the peroxylactic acid is further beneficial for micro efficacy.

These results further indicate that various high and lower temperature applications of use are suitable for use with the peroxyhydroxycarboxylic acids, namely the high micro efficacy of the peroxylactic acid.

Example 10

Additional antimicrobial efficacy of generated peroxylactic acid was evaluated following the US EPA food contact suspension test protocol (AOAC 960.09) against *Salmonella, E. coli, Campylobacter* and *Listeria* according to the conditions set forth in Table 16.

TABLE 16

| | Test Parameters |
|---|---|
| Test System: | *Salmonella* ser. Heidelberg, Newport and Braenderup (modified to be resistant to 50 µg/mL nalidixic acid) |
| | *Escherichia coli* ATCC 11229 |
| | *Campylobacter jejuni* ATCC 33291 |
| | *Listeria monocytogenes* ATCC 49594 |
| Test Substance Diluent: | 500 ppm Synthetic Hard Water, pH 7.71 |
| Test Substances: | 25 ppm PLA |
| | 50 ppm PLA |
| | 100 ppm PLA |
| Exposure Time (seconds): | 30 seconds |
| Neutralizer: | 9 mL DE Broth |
| Test Temperature: | Ambient (18-20° C.) |
| Plating Medium: | TSA |
| Incubation: | 35° C. for 48 hours |

Figure 7:
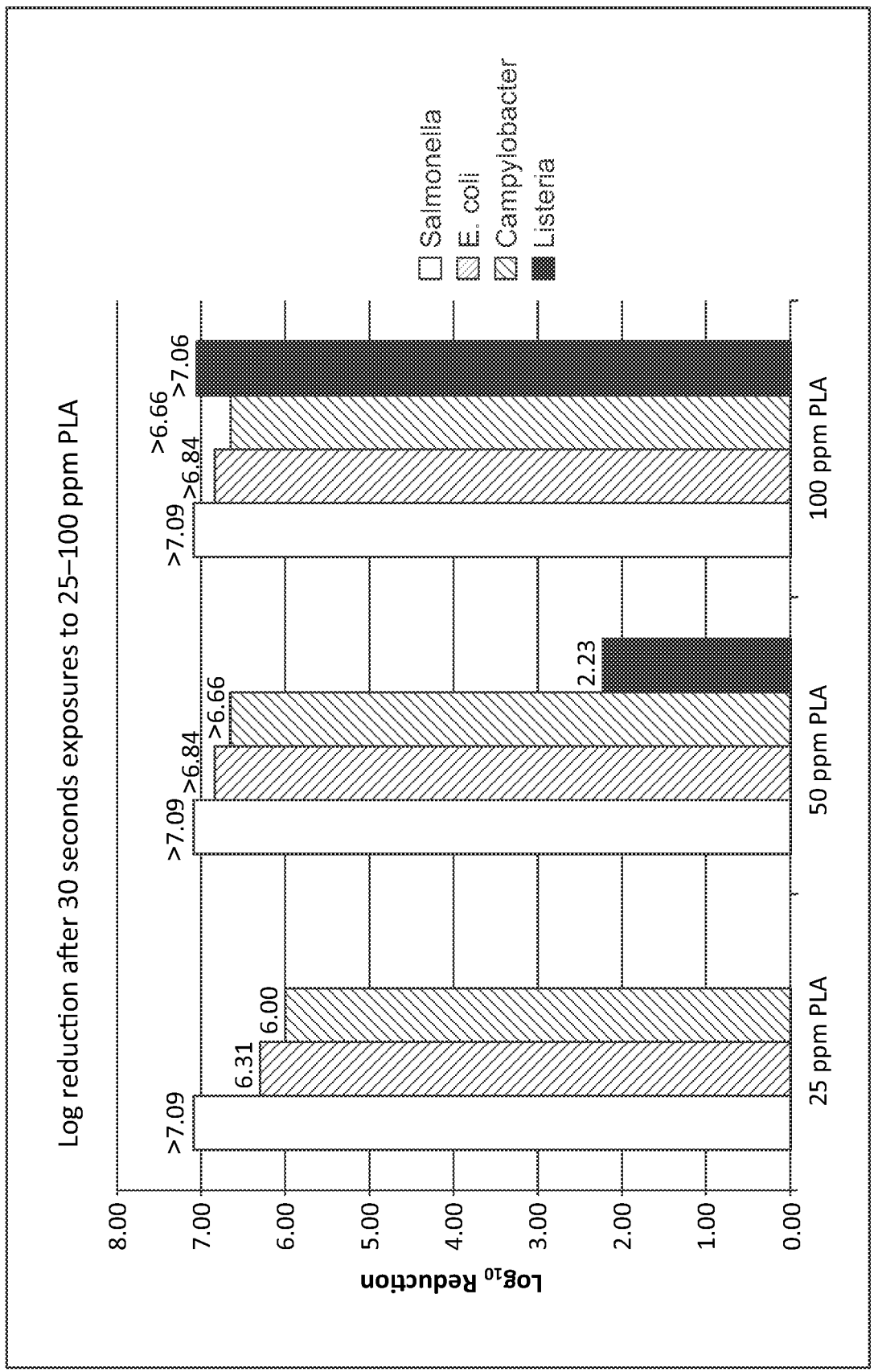
FIG. 7 shows efficacy of peroxylactic acid at low concentrations, particularly against *Listeria*.

The results are shown in FIG. 7, demonstrating that PLA provides efficacy at low concentration doses (as low as 25 ppm) against various microbes. In addition at 100 ppm PLA provides efficacy of greater than 7 log reduction against *Listeria*, whereas peroxyacetic acid is known to require at least about 180 ppm for greater than 7 log reduction against *Listeria*.

Example 11

Figure 8:
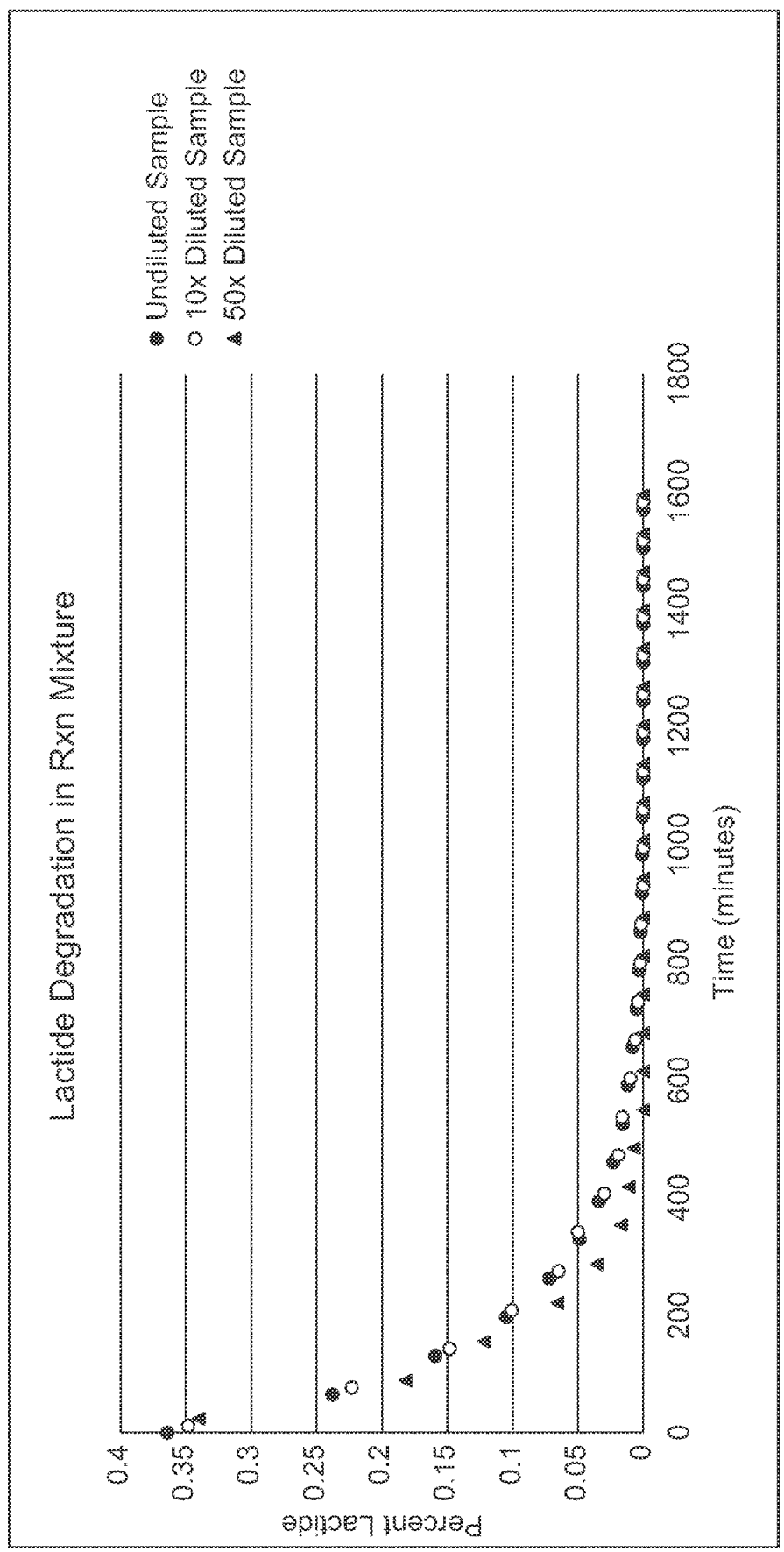
FIG. 8 shows the kinetics of lactide degradation over time.
Figure 9:
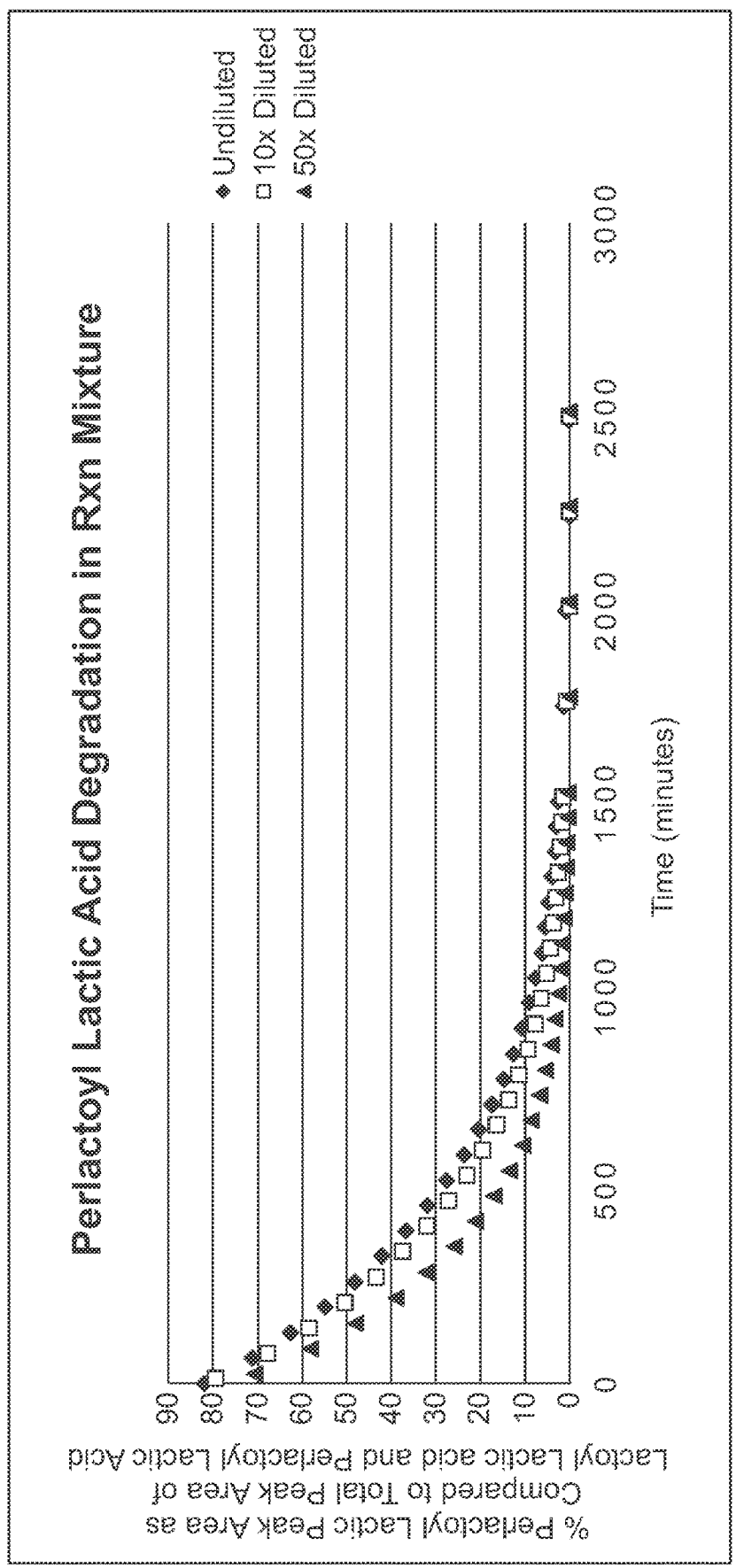
FIG. 9 shows the kinetics of peroxylactoyllactic acid degradation over time (from lactic or lactide).

Additional testing to confirm the degradation of the perlactoyllactic acid compared to degradation of the lactide precursor were monitored by HPLC. FIG. 8 shows the kinetics of lactide degradation over time comparing undiluted to 10× and 50× diluted samples. FIG. 9 shows the kinetics of perlactoyllactic acid degradation over time comparing undiluted to 10× and 50× diluted samples. Beneficially, the peroxylactoyllactic acid and peroxylactic acid degrade into lactic acid, a food safe ingredient.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. In addition, the contents of all patent publications discussed supra are incorporated in their entirety by this reference.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The invention claimed is:

1. A peroxyhydroxycarboxylic acid forming composition comprising:
    a) a first reagent that comprises a lactone of an alphahydroxycarboxylic acid, and
    b) a second reagent that comprises an alkalinity source,
    c) a third reagent that comprises hydrogen peroxide; and
    d) optionally water or a solvent if the first, second and/or third reagents are powders;
    wherein said reagents are provided as powders and/or liquids, and wherein the powder reagents are combined into a premix and the liquid reagents are kept separately from the powder reagents prior to contacting to generate the peroxyhydroxycarboxylic acid; and
    wherein the combination of the reagents react to form a liquid that comprises the peroxyhydroxycarboxylic acid and has a pH below about 7 within about 5 minutes after the contact between said reagent.

2. The peroxyhydroxycarboxylic acid forming composition of claim 1, wherein the lactone of the alphahydroxycarboxylic acid is a diester of lactone.

3. The peroxyhydroxycarboxylic acid forming composition of claim 2, wherein the alphahydroxycarboxylic acid is lactic acid or glycolic acid, and wherein the lactone of the alphahydroxycarboxylic acid is correspondingly lactide or glycolide.

4. The peroxyhydroxycarboxylic acid forming composition of claim 1, wherein the alkalinity source comprises an alkaline metal hydroxide, an alkali metal silicate, an alkali metal carbonate, borates, amines, amides or other basic nitrogen sources or mixtures thereof.

5. The peroxyhydroxycarboxylic acid forming composition of claim 1, wherein the reagents are contacted to form a liquid solution comprising the peroxyhydroxycarboxylic acid in amounts from about 0.1 ppm to about 100,000 ppm, and/or wherein the peroxyhydroxycarboxylic acid has less than about 1 Kpa vapor pressure at 20° C.

6. The peroxyhydroxycarboxylic acid forming composition of claim 1, further comprising a catalyst or an enzyme that catalyzes formation of the peroxyhydroxycarboxylic acid, wherein the catalyst or enzyme comprises a perhydrolytic enzyme, lipase, coronase, termanyl or esperease.

7. The peroxyhydroxycarboxylic acid forming composition of claim 1, further comprising a stabilizing agent and/or a pH buffering agent.

8. The peroxyhydroxycarboxylic acid forming composition of claim 1, further comprising an additional-C1-C22 peroxycarboxylic acid.

9. The peroxyhydroxycarboxylic acid forming composition of claim 1, further comprising an ester precursor and/or a carboxylic acid precursor of an additional-C1-C22 peroxycarboxylic acid.

10. A method for treating a target, which method comprises contacting a target with an effective amount of peroxyhydroxycarboxylic acid according to claim 1 to form a treated target composition, wherein said treated target composition comprises from about 0.1 ppm to about 10,000 ppm of said peroxyhydroxycarboxylic acid, and said contacting lasts for sufficient time to bleach, remove soils, disinfect and/or stabilize or reduce microbial population in and/or on said target or said treated target composition.

11. The method of claim 10, wherein the target is a surface in need of high-level disinfecting and the method comprises providing an effective amount of the peroxyhydroxycarboxylic acid to the surface in need of treatment, wherein said treated surface source comprises from about 1 ppm to about 1,000 ppm of said peroxyhydroxycarboxylic acid.

12. The method of claim 10, wherein the contacting step lasts for about 1 second to about 10 minutes.

13. The method of claim 10, wherein the contacting step is conducted at a temperature ranging from about 0° C. to about 70° C.

14. The method of claim 10, wherein the target is a food item or a plant item and/or at least a portion of a medium, a container, an equipment, a system or a facility for growing, holding, processing, packaging, storing, transporting, preparing, cooking or serving the food item or the plant item and wherein the treatment does not induce an organoleptic effect in and/or on the food item or a plant item.

15. The method of claim 10, wherein the target is at least a portion of a medium, a container, an equipment, a system or a facility for producing, holding, processing, packaging, storing, or transporting pulp, and is used in papermaking, textiles, food, or pharmaceutical industry.

16. The method of claim 10, wherein the target is a water source and/or a biofilm.

17. The method of claim 10, wherein the target is at least a portion of a medium, a surface, a container, an equipment, or a system in a health care facility and/or wherein the target is a medical instrument in need of repurposing or reprocessing.

18. The method of claim 10, wherein the target is a laundry article and wherein the laundry article is soiled and contacted by the peroxyhydroxycarboxylic acid in a conventional laundry application, a pre-wash step, a pre-bleach step and/or outside of a washing machine.

19. The method of claim 10, wherein the peroxyhydroxycarboxylic acid is saturated onto a wipe.

20. The method of claim 10, wherein one or more of the reagents to generate the peroxyhydroxycarboxylic acid is saturated onto a wipe.

* * * * *